(12) United States Patent
Zugibe et al.

(10) Patent No.: US 8,463,441 B2
(45) Date of Patent: *Jun. 11, 2013

(54) METHOD AND APPARATUS FOR OPTIMIZING REFRIGERATION SYSTEMS

(75) Inventors: Kevin Zugibe, New City, NY (US); Riyaz Papar, The Woodlands, TX (US)

(73) Assignee: Hudson Technologies, Inc., Pearl River, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 13/280,302

(22) Filed: Oct. 24, 2011

(65) Prior Publication Data
US 2012/0041608 A1 Feb. 16, 2012

Related U.S. Application Data

(60) Continuation of application No. 12/565,147, filed on Sep. 23, 2009, now Pat. No. 8,046,107, which is a division of application No. 10/730,791, filed on Dec. 9, 2003, now Pat. No. 7,599,759.

(60) Provisional application No. 60/431,901, filed on Dec. 9, 2002, provisional application No. 60/434,847, filed on Dec. 19, 2002.

(51) Int. Cl.
*G01M 1/38* (2006.01)
*G05D 9/00* (2006.01)
*F25B 41/00* (2006.01)

(52) U.S. Cl.
USPC .............................. 700/275; 700/28; 62/209

(58) Field of Classification Search
USPC ........ 700/28–31, 275, 281, 282; 62/207–209, 62/214, 215, 226–230; 712/233, 241
See application file for complete search history.

(56) References Cited

U.S. PATENT DOCUMENTS

| | | | | | |
|---|---|---|---|---|---|
| 4,325,223 | A | * | 4/1982 | Cantley | 62/126 |
| 5,203,177 | A | * | 4/1993 | Manz et al. | 62/149 |
| 5,295,362 | A | * | 3/1994 | Shaw et al. | 62/193 |
| 5,392,612 | A | * | 2/1995 | Alsenz | 62/115 |
| 5,428,966 | A | * | 7/1995 | Alsenz | 62/116 |

(Continued)

FOREIGN PATENT DOCUMENTS

JP 62 200153 A 9/1987

OTHER PUBLICATIONS

European Search Report 03812911.0—2311/1585924 PCT/US0339175, dated Sep. 12, 2000.

*Primary Examiner* — M. N. Von Buhr
(74) *Attorney, Agent, or Firm* — Steven M. Hoffberg; Ostrolenk Faber LLP

(57) ABSTRACT

A control system for controlling a refrigeration system having an operating point, comprising: a memory configured to store a relationship of at least an evaporator efficiency, an evaporator heat load, a refrigerant amount in the evaporator, and a variable dependent on a non-volatile liquid mixed with refrigerant in the evaporator an input port configured to receive a signal corresponding to at least a measured evaporator heat load during operation; an output port configured to present an output to selectively alter an operating point of the evaporator, by altering the refrigerant amount in the evaporator and thereby changing the variable; and a processor, configured to receive the signal, access the memory; and generate the output to selectively move toward an optimum operating point. A corresponding method and refrigeration system are provided.

20 Claims, 8 Drawing Sheets

U.S. PATENT DOCUMENTS

| | | | |
|---|---|---|---|
| 5,669,225 A * | 9/1997 | Beaverson et al. | 62/201 |
| 5,711,159 A * | 1/1998 | Whipple, III | 62/82 |
| 5,761,914 A * | 6/1998 | Carey et al. | 62/84 |
| 5,782,103 A * | 7/1998 | Schmidt | 62/225 |
| 5,809,795 A * | 9/1998 | Beaverson et al. | 62/218 |
| 5,875,637 A | 3/1999 | Paetow | |
| 5,937,659 A * | 8/1999 | Weyna et al. | 62/84 |
| 5,966,954 A * | 10/1999 | Arima et al. | 62/185 |
| 6,079,220 A * | 6/2000 | Buck | 62/212 |
| 6,082,981 A * | 7/2000 | Nakajima et al. | 418/55.6 |
| 6,092,380 A * | 7/2000 | Kachur et al. | 62/228.3 |
| 6,237,362 B1 * | 5/2001 | Jang | 62/469 |
| 6,244,055 B1 * | 6/2001 | Hanson et al. | 62/85 |
| 6,257,324 B1 * | 7/2001 | Osakabe et al. | 165/104.33 |
| 6,505,475 B1 * | 1/2003 | Zugibe et al. | 62/192 |
| 6,619,061 B2 * | 9/2003 | Beaverson et al. | 62/201 |
| 6,705,094 B2 * | 3/2004 | Alsenz | 62/116 |
| 6,973,410 B2 * | 12/2005 | Seigel | 702/182 |
| 7,059,143 B1 * | 6/2006 | Zugibe et al. | 62/192 |
| 7,082,380 B2 * | 7/2006 | Wiebe et al. | 702/182 |
| 7,086,240 B1 * | 8/2006 | Zugibe et al. | 62/114 |
| 7,139,564 B2 * | 11/2006 | Hebert | 455/423 |
| 7,349,824 B2 * | 3/2008 | Seigel | 702/182 |
| 7,533,536 B1 * | 5/2009 | Zugibe et al. | 62/127 |
| 7,599,759 B2 * | 10/2009 | Zugibe et al. | 700/275 |
| 7,805,952 B1 * | 10/2010 | Zugibe et al. | 62/84 |
| 8,046,107 B2 * | 10/2011 | Zugibe et al. | 700/275 |

* cited by examiner

METHOD AND APPARATUS FOR OPTIMIZING REFRIGERATION SYSTEMS

RELATED APPLICATIONS

The present application is a Continuation of U.S. patent application Ser. No. 12/565,147, filed Sep. 23, 2009, now U.S. Pat. No. 8,046,107, issued Oct. 25, 2011, which is a Division of U.S. patent application Ser. No. 10/730,791, filed Dec. 9, 2003, now U.S. Pat. No. 7,599,759, issued Oct. 6, 2009, each of which is expressly incorporated herein by reference, which claims benefit of priority from U.S. Provision Patent Application No. 60/431,901, filed Dec. 9, 2002, and 60/434,847, filed Dec. 19, 2002, each of which is expressly incorporated herein by reference.

FIELD OF THE INVENTION

The present invention relates to the field of methods and systems for optimization of refrigeration system operation.

BACKGROUND OF THE INVENTION

In large industrial scale systems, efficiency may be a critical aspect of operations. Even small improvement of system efficiency can lead to significant cost savings; likewise, loss of efficiency may lead to increased costs or even system failure. Chillers represent a significant type of industrial system, since they are energy intensive to operate, and are subject to variation of a number of parameters which influence system efficiency and capacity.

The vast majority of mechanical refrigeration systems operate according to similar, well known principles, employing a closed-loop fluid circuit through which refrigerant flows, with a source of mechanical energy, typically a compressor, providing the motive forces for pumping heat from an evaporator to a condenser. In a chiller, water or brine is cooled in the evaporator for use in a process. In a common type of system, discussed in more detail below, the evaporator is formed as a set of parallel tubes, forming a tube bundle, within a housing. The tubes end on either side in a separator plate. The water or brine flows through the tubes, and the refrigerant is separately provided on the outside of the tubes, within the housing.

The condenser receives hot refrigerant gas from the compressor, where it is cooled. The condenser may also have tubes, which are, for example, filled with water which flows to a cooling tower. The cooled refrigerant condenses as a liquid, and flows by gravity to the bottom of the condenser, where it is fed through a valve or orifice to the evaporator.

The compressor therefore provides the motive force for active heat pumping from the evaporator to the condenser. The compressor typically requires a lubricant, in order to provide extended life and permit operation with close mechanical tolerances. The lubricant is an oil which miscible with the refrigerant. Thus, an oil sump is provided to feed oil to the compressor, and a separator is provided after the compressor to capture and recycle the oil. Normally, the gaseous refrigerant and liquid lubricant are separated by gravity, so that the condenser remains relatively oil free. However, over time, lubricating oil migrates out of the compressor and its lubricating oil recycling system, into the condenser. Once in the condenser, the lubricating oil becomes mixed with the liquefied refrigerant and is carried to the evaporator. Since the evaporator evaporates the refrigerant, the lubricating oil accumulates at the bottom of the evaporator.

The oil in the evaporator tends to bubble, and forms a film on the walls of the evaporator tubes. In some cases, such as fin tube evaporators, a small amount of oil enhances heat transfer and is therefore beneficial. In other cases, such as nucleation boiling evaporator tubes, the presence of oil, for example over 1%, results in reduced heat transfer. See, Schlager, L. M., Pate, M. B., and Berges, A. E., "A Comparison of 150 and 300 SUS Oil Effects on Refrigerant Evaporation and Condensation in a Smooth Tube and Micro-fin Tube", ASHRAE Trans. 1989, 95(1):387-97; Thome, J. R., "Comprehensive Thermodynamic Approach to Modelling Refrigerant-Lubricating Oil Mixtures", Intl. J. HVAC&R Research (ASHRAE) 1995, 110-126; Poz, M. Y., "Heat Exchanger Analysis for Nonazeotropic Refrigerant Mixtures", ASHRAE Trans. 1994, 100(1) 727-735 (Paper No. 95-5-1).

A refrigeration system is typically controlled at a system level in one of two ways: by regulating the temperature of the gas phase in the top of the evaporator (the superheat), or by seeking to regulate the amount of liquid (liquid level) within the evaporator. As the load on the system increases, the equilibrium within the evaporator changes. Higher heat load will increase temperatures in the headspace Likewise, higher load will boil more refrigerant per unit time, and lead to lower liquid levels.

For example, U.S. Pat. No. 6,318,101, expressly incorporated herein by reference, relates to a method for controlling an electric expansion valve based on cooler pinch and discharge superheat. This system seeks to infer the level of refrigerant in the evaporator and control the system based thereon, while preventing liquid slugging. A controlled monitors certain variables which are allegedly used to determine the optimal position of the electronic expansion valve, to optimize system performance, the proper discharge superheat value, and the appropriate refrigerant charge. See also, U.S. Pat. No. 6,141,980, expressly incorporated herein by reference.

U.S. Pat. No. 5,782,131, expressly incorporated herein by reference, relates to a refrigeration system having a flooded cooler with a liquid level sensor.

Each of these strategies provides a single fixed setpoint which is presumed to be the normal and desired setpoint for operation. Based on this control variable, one or more parameters of operation are varied. Typically, a compressor will either have a variable speed drive or a set of variable angle vanes which deflect gaseous refrigerant from the evaporator to the compressor. These modulate the compressor output. Additionally, some designs have a controllable expansion valve between the condenser and evaporator. Since there is a single main control variable, the remaining elements are controlled together as an inner loop to maintain the control variable at the setpoint.

Typical refrigerants are substances that have a boiling point (at the operating pressure) below the desired cooling temperature, and therefore absorb heat from the environment while evaporating (changing phase) under operational conditions. Thus, the evaporator environment is cooled, while heat is transferred to another location, the condenser, where the latent heat of vaporization is shed. Refrigerants thus absorb heat via evaporation from one area and reject it via condensation into another area. In many types of systems, a desirable refrigerant provides an evaporator pressure as high as possible and, simultaneously, a condenser pressure as low as possible. High evaporator pressures imply high vapor densities, and thus a greater system heat transfer capacity for a given compressor. However, the efficiency at the higher pressures is lower, especially as the condenser pressure approaches the critical pressure of the refrigerant.

The overall efficiency of the refrigeration system is influenced by the heat transfer coefficients of the respective heat exchangers. Higher thermal impedance results in lower efficiency, since temperature equilibration is impaired, and a larger temperature differential must be maintained to achieve the same heat transfer. The heat transfer impedance generally increases as a result of deposits on the walls of the heat exchangers, although, in some cases, heat transfer may be improved by various surface treatments and/or an oil film.

Refrigerants must satisfy a number of other requirements as best as possible including: compatibility with compressor lubricants and the materials of construction of refrigerating equipment, toxicity, environmental effects, cost availability, and safety. The fluid refrigerants commonly used today typically include halogenated and partially halogenated alkanes, including chlorofluorocarbons (CFCs), hydrochlorofluorocarbons (HFCFs), and less commonly hydrofluorocarbons (HFCs) and perfluorocarbons (PFCs). A number of other refrigerants are known, including propane and fluorocarbon ethers. Some common refrigerants are identified as R11, R12, R22, R500, and R502, each refrigerant having characteristics that make them suitable for different types of applications.

In an industrial chiller, the evaporator heat exchanger is a large structure, containing a plurality of parallel tubes in a bundle, within a larger vessel comprising a shell. The liquid refrigerant and oil form a pool in the bottom of the evaporator, boiling and cooling the tubes and their contents. Inside the tubes, an aqueous medium, such as brine, circulates and is cooled, which is then pumped to another region where the brine cools the industrial process. Such an evaporator may hold hundreds or thousands of gallons of aqueous medium with an even larger circulating volume. Since evaporation of the refrigerant is a necessary part of the process, the liquid refrigerant and oil must fill only part of the evaporator.

It is also known to periodically purge a refrigeration or chiller system, recycling purified refrigerant through the system to clean the system. This technique, however, generally permits rather large variance in system efficiency and incurs relatively high maintenance costs. Further, this technique generally does not acknowledge that there is an optimum (non-zero) level of oil in the evaporator and, for example, the condenser. Thus, typical maintenance seeks to produce a "clean" system, which may be suboptimal, subject to incremental changes after servicing. Refrigerant from a refrigeration system may be reclaimed or recycled to separate oil and provide clean refrigerant, in a manual process that requires system shutdown.

U.S. Pat. No. 6,260,378, expressly incorporated herein by reference, relates to a refrigerant purge system, in particular to control removal of non-condensable gases.

The oil in the evaporator tends to accumulate, since the basic design has no inherent path for returning the oil to the sump. For amounts in excess of the optimum, there are generally reduced system efficiencies resulting from increasing oil concentration in the evaporator. Thus, buildup of large quantities of refrigerant oil within an evaporator will reduce efficiency of the system.

In-line devices may be provided to continuously remove refrigerant oil from the refrigerant entering the evaporator. These devices include so-called oil eductors, which remove oil and refrigerant from the evaporator, returning the oil to the sump and evaporated refrigerant to the compressor. The inefficiency of these continuous removal devices is typically as a result of the bypassing of the evaporator by a portion of the refrigerant, and potentially a heat source to vaporize or partially distill the refrigerant to separate the oil. Therefore, only a small proportion of the refrigerant leaving the condenser may be subjected to this process, resulting in poor control of oil level in the evaporator and efficiency loss. There is no adequate system for controlling the eductor. Rather, the eductor may be relatively undersize and run continuously. An oversize eductor would be relatively inefficient, since the heat of vaporization is not efficiently used in the process.

Another way to remove oil from the evaporator is to provide a shunt for a portion of mixed liquid refrigerant and oil in the evaporator to the compressor, wherein the oil is subject to the normal recycling mechanisms. This shunt, however, may be inefficient and is difficult to control. Further, it is difficult to achieve and maintain low oil concentrations using this method.

U.S. Pat. No. 6,233,967, expressly incorporated herein by reference, relates to a refrigeration chiller oil recovery system which employs high pressure oil as an eductor motive fluid. See also, U.S. Pat. Nos. 6,170,286 and 5,761,914, expressly incorporated herein by reference.

In both the eductor and shunt, as the oil level reaches low levels, e.g., about 1%, 99% of the fluid being separate is refrigerant, leading to significant loss of process efficiency.

It is noted that it is difficult to accurately sample and determine the oil concentration in the evaporator. As the refrigerant boils, oil concentration increases. Therefore, the oil concentration near the top of the refrigerant is higher than the bulk. However, as the boiling liquid churns, inhomogeneities occur, and accurate sampling becomes difficult or impossible. Further, it is not clear that the average bulk oil concentration is a meaningful control variable, apart from the effects of the oil on the various components. Since it is difficult to measure the oil concentration, it is also difficult to measure the amount of refrigerant in the evaporator. A difficulty of measurement of the amount of refrigerant is compounded by the fact that, during operation, the evaporator is boiling and froths; measuring the amount during a system shutdown must account for any change in distribution of the refrigerant between the other system components.

It is known that the charge conditions of a chiller may have a substantial effect on both system capacity and system operating efficiency. Obviously, if the amount of liquid refrigerant in the evaporator is insufficient, the system cannot meet its cooling needs, and this limits capacity. Thus, in order to handle a larger heat load, a greater quantity of refrigerant, at least in the evaporator, is required. However, in typical designs, by providing this large refrigerant charge, the operating efficiency of the system at reduced loads is reduced, thus requiring more energy for the same BTU cooling. Bailey, Margaret B., "System Performance Characteristics of a Helical Rotary Screw Air-Cooled Chiller Operating Over a Range of Refrigerant Charge Conditions", ASHRAE Trans. 1998 104(2), expressly incorporated herein by reference. Therefore, by correctly selecting the "size" (e.g., cooling capacity) of the chiller, efficiency is enhanced. Typically the chiller capacity is determined by the maximum expected design load, and thus for any given design load, the quantity of refrigerant charge in a typical design is dictated. Therefore, in order to achieve improved system efficiency, a technique of modulation recruitment is employed, in which one or more of a plurality of subsystems are selectively activated depending on the load, to allow efficient design of each subsystem while permitting a high overall system load capacity with all subsystems operational. See, Trane "Engineer's Newsletter" December 1996, 25(5):1-5. Another known technique seeks to alter the rotational speed of the compressor. See, U.S. Pat. No. 5,651,264, expressly incorporated herein by reference. It is also possible to control compressor speed using an electronic motor control, or system capacity, by restricting refrigerant flow into the compressor.

Chiller efficiency generally increases with chiller load. Thus, an optimal system seeks to operate system near its rated design. Higher refrigerant charge level than the nominal full level, however, results in deceased efficiency. Further, chiller load capacity sets a limit on the minimum refrigerant charge level. Therefore, it is seen that there exists an optimum refrigerant charge level for maximum efficiency. As stated above, as oil level increases in the evaporator, it both displaces refrigerant and has an independent effect on system efficiency.

Systems are available for measuring the efficiency of a chiller, i.e., a refrigeration system which cools water or a water solution, such as brine. In these systems, the efficiency is calculated based on Watt-hours of energy consumed (Volts×Amps×hours) per cooling unit, typically tons or British Thermal Unit (BTU) (the amount of energy required to change the temperature of one British ton of water 1° C.). Thus, a minimal measurement of efficiency requires a power meter (timebase, voltmeter, ammeter), and thermometers and flowmeters for the inlet and outlet water. Typically, further instruments are provided, including a chiller water pressure gage, gages for the pressure and temperature of evaporator and condenser. A data acquisition system processor is also typically provided to calculate the efficiency, in BTU/kWH.

U.S. Pat. Nos. 4,437,322; 4,858,681; 5,653,282; 4,539,940; 4,972,805; 4,382,467; 4,365,487; 5,479,783; 4,244,749; 4,750,547; 4,645,542; 5,031,410; 5,692,381; 4,071,078; 4,033,407; 5,190,664; and 4,747,449, expressly incorporated herein by reference, relate to heat exchangers and the like.

There are a number of known methods and apparatus for separating refrigerants, including U.S. Pat. Nos. 2,951,349; 4,939,905; 5,089,033; 5,110,364; 5,199,962; 5,200,431; 5,205,843; 5,269,155; 5,347,822; 5,374,300; 5,425,242; 5,444,171; 5,446,216; 5,456,841; 5,470,442; 5,534,151; and 5,749,245, expressly incorporated herein by reference. In addition, there are a number of known refrigerant recovery systems, including U.S. Pat. Nos. 5,032,148; 5,044,166; 5,167,126; 5,176,008; 5,189,889; 5,195,333; 5,205,843; 5,222,369; 5,226,300; 5,231,980; 5,243,831; 5,245,840; 5,263,331; 5,272,882; 5,277,032; 5,313,808; 5,327,735; 5,347,822; 5,353,603; 5,359,859; 5,363,662; 5,371,019; 5,379,607; 5,390,503; 5,442,930; 5,456,841; 5,470,442; 5,497,627; 5,502,974; 5,514,595; and 5,934,091, expressly incorporated herein by reference. Also known are refrigerant property analyzing systems, as shown in U.S. Pat. Nos. 5,371,019; 5,469,714; and 5,514,595, expressly incorporated herein by reference.

SUMMARY OF THE INVENTION

The present invention provides a system and method for optimizing operation of a refrigeration system.

In most known refrigeration systems, control is exerted principally to assure that liquid refrigerant is not returned to the compressor, and otherwise to assure that the level of refrigerant in the evaporator is presumed to be at a predetermined set level.

According to the present invention, the optimum level of refrigerant and oil in the evaporator is not predetermined. Rather, it is understood that, over time, the system characteristics may change, as well as the load characteristics, and that an optimal control requires more complexity. Likewise, it is understood that direct measurements of the effective levels of relevant parameters may not be measurable, and thus surrogates may be provided.

According to the present invention, a pair of control loops, an inner loop and an outer loop, are provided. The inner loop controls the compressor, than is, the motive force for pumping heat. This inner control loop receives a single input from the outer loop, and optimizes the compressor operation in accordance therewith, for example compressor speed, duty cycle, inlet vane position, and the like. If present, a controllable expansion valve (typically located between the condenser and evaporator) is also encompassed within this inner control loop. Thus, the inner control loop controls the rate of supply of liquid refrigerant to the evaporator.

The outer control loop controls the partitioning of refrigerant between the evaporator and a refrigerant accumulator element within the system. The accumulator is typically not a "functional" system element, in that the amount of refrigerant in the accumulator is not critical, simply that this element allows a variation in the amount of refrigerant elsewhere in the system. The accumulator may be a lower portion of the condenser, a separate accumulator, or even a reserve portion of the evaporator which does not significantly particulate in the cooling process.

During steady state operation, the feed of liquid refrigerant from the condenser will equal the rate of gaseous intake to the compressor. Thus, the rate of heat absorption in the evaporator will effectively control the inner control loop for the compressor. Typically, this heat absorption may be measured or estimated from a variety of system sensors, including evaporator discharge temperature and pressure, evaporator water/brine inlet and outlet temperature and pressure, and possibly condenser headspace temperature and pressure.

The outer control loop determines an optimal level of refrigerant in the evaporator. A direct measurement of refrigerant level in the evaporator is difficult for two reasons: First, the evaporator is filled with refrigerant and oil, and a direct sampling of the evaporator contents, such as by using an optical sensor for oil concentration, does not typically yield useful results during system operation. During system shutdown, the oil concentration may be accurately measured, but such shutdown conditions typically allow a repartitioning of refrigerant within the various system components. Second, during operation, the refrigerant and oil bubble and froth, and therefore there is no simple level to be determined. Rather a preferred method for inferring the amount of refrigerant in the evaporator, especially changes over a relatively short period of time, is to monitor the level of refrigerant in the accumulator, which is preferably a lower portion of the condenser or associated with the condenser. Since this refrigerant is relatively pure, and held under condensing conditions, the level is relatively easy to measure. Since the remaining system components include principally refrigerant gas, a measurement of the condenser or accumulator refrigerant level will provide useful information for measuring changes in evaporator refrigerant level. If the starting levels of both the accumulator or condenser and evaporator are known (even during a shutdown state), than an absolute measurement may be calculated.

Of course, there are other means for measuring or calculating the amount of refrigerant in the evaporator, and broad embodiments of the invention are not limited to the preferred method of measurement.

The present invention provides, however, that there is a partitioning of refrigerant, with variable control over the amount within the evaporator. The outer loop controls this level to achieve an optimum state.

In a refrigeration system, efficiency is calculated in terms of energy per unit heat transfer. Energy may be supplied as electricity, gas, coal, steam, or other source, and may be directly measured. Surrogate measurements may also be employed, as known in the art. Heat transfer may also be calculated in known manner. For example, the heat transfer to the cooled process water is calculated by measuring or estimating the flow rate and the inlet and outlet temperatures.

While it is possible to map the control algorithm in terms of desired partitioning of refrigerant under a variety of load circumstances, a preferred embodiment of the invention provides an adaptive control. This adaptive control determines, during system transients, which may be normally occurring or induced, the charge in system efficiency with changes in refrigerant partitioning at a given operating point. For example, if the process changes, requiring a different heat load dissipation, this will be represented by a change in inlet water temperature and/or flow rate. This change will result in a different rate of refrigerant evaporation in the evaporator, and thus a transient change in partitioning. Before or in conjunction with correcting the refrigerant partitioning, the control monitors the system efficiency. This monitoring allows the control to develop a system model, which then allows it to anticipate an optimum control surface. The outer loop reparations the refrigerant to achieve optimum efficiency. It is noted that, while efficiency is typically considered to be kW/ton, other measurements of efficiency may be substituted without materially altering the control strategy. For example, instead of optimizing the refrigeration system itself, the industrial process may be included. In this case, the production parameters or economics of the process may be calculated, to provide a more global optimization.

In a global optimization, other systems may also require control or serve as inputs. These may be accommodated in known manner.

Over time, oil migrates from the oil sump of the compressor to the evaporator. One aspect of the invention provides a control system which measures oil consumption, in order to estimate oil level in the evaporator. This control system therefore measures oil replenishment into the sump, oil return from the outlet of the compressor, and oil return from the eductor. It is noted that the oil in the sump may be mixed with refrigerant, and therefore a simple level gage will likely require compensation, such as by boiling a sample of oil to remove refrigerant, or by using an oil concentration sensor, such as an optical type sensor. Thus, it is possible to estimate the amount of oil migration into the evaporator, and with a known starting state or clean system, to estimate a total amount of oil. Using measurements of evaporator discharge temperature and pressure, as well as water inlet and outlet temperature and pressure, it is further possible to estimate heat transfer coefficients in the tube bundle, and impairments thereof. The refrigerant, oil and heat transfer impairments are the principle internal variables which control the efficiency of the evaporator. Over the short term (and assuming that oil is not intentionally added to the evaporator), refrigerant is the only effective and available control variable. Over longer periods, an oil eductor may be controlled based on inferred or measured oil concentration to return the oil level in the evaporator to an optimal level. Over extended intervals, maintenance may be performed to correct heat transfer impairments and purify the refrigerant. Such maintenance requirements may be indicated as an output from the control system. For example, the control system operates automatically to immediately tune the control variable to an optimum state. This tuning is triggered by a change in process conditions or some adaptive auto-tuning process. In addition, overtime, the optimization control surface will vary. As this surface varies to reduce overall efficiency, secondary correction controls may be invoked, such as oil eductor, non-condensable gas purge (typically from the condenser), or the like. Over a longer term, the control may model significant parameters of system operation with respect to a model, and determine when a service is required, either because the system is failing, or substantial inefficiencies are apparent, such as impaired heat transfer through the tube bundle.

As stated above, the inner control loop is generally insulated from direct response to changes in process. Further, since the evaporator is generally outside of the inner control loop, this control loop generally does not suffer adverse changes over time, except buildup of non-condensable gasses in the condenser, which are relatively easy to infer based on a superheat value, and relatively easy to purge. Thus, the inner control loop may typically operate according to a predetermined control strategy, and need not be adaptive. This, in turn, allows multivariate control, for example, motor speed, inlet vane position, and expansion valve control, to be effected based on a static system model, to achieve optimal efficiency under a variety of conditions.

On the other hand, the outer control loop seeks to control the short term system response principally based on an optimization of a single variable, refrigerant partitioning, with variations in system load. While a static system model is difficult or impossible to implement, while achieving the required accuracy, such a control is readily implemented in an adaptive fashion, to compensate for changes in the system, and indeed, over a period of time, to correct deviations in system parameters which adversely effect system efficiency.

It is, of course, apparent that these control loops and their algorithmic implementation may be merged, and indeed hybridized, the general strategy remains the same. At any operating point, the partitioning of refrigerant is controlled to achieve a maximum efficiency. The system senses or tests efficiency as a function of the control variable, in order to compensate for changes in system response.

A more detailed analysis of the basis for refrigerant partitioning as a control strategy is provided. Chiller efficiency depends on several factors, including subcooling temperature and condensing pressure, which, in turn, depend on the level of refrigerant charge, nominal chiller load, and the outdoor air temperature. First, subcooling within the thermodynamic cycle will be examined. FIG. 6A shows a vapor compression cycle schematic and FIG. 6B shows an actual temperature-entropy diagram, wherein the dashed line indicates an ideal cycle. Upon exiting the compressor at state 2, as indicated in FIG. 6A, a high-pressure mixture of hot gas and oil passes through an oil separator before entering the tubes of the remote air-cooled condenser where the refrigerant rejects heat (Qh) to moving air by forced convection (or other cooling medium). In the last several rows of condenser coils, the high-pressure saturated liquid refrigerant should be subcooled, e.g., 10 F to 20 F (5.6 C to 11.1 C), according to manufacturer's recommendations, as shown by state 3 in FIG. 6B. This level of subcooling allows the device following the condenser, the electronic expansion valve, to operate properly. In addition, the level of subcooling has a direct relationship with chiller capacity. A reduced level of subcooling results in a shift of state 3 (in FIG. 6B) to the right and a corresponding shift of state 4 to the right, thereby reducing the heat removal capacity of the evaporator (Q1).

As the chiller's refrigerant charge increases, the accumulation of refrigerant stored in the condenser on the high-pressure side of the system also increases. An increase in the amount of refrigerant in the condenser also occurs as the load on the chiller decreases due to less refrigerant flow through the evaporator, which results in increased storage (accumulation) in the condenser. A flooded condenser causes an increase in the amount of sensible heat transfer area used for subcooling, and a corresponding decrease in the surface area used for latent or isothermal heat transfer associated with condensing. Therefore, increasing refrigerant charge level and decreasing chiller load both result in increased subcooling temperatures and condensing temperatures.

According to the present invention, therefore, the condenser or accumulator are provided to reduce any inefficiency resulting from variable storage of the refrigerant. This can be achieved by a static mechanical configuration, or a controlled variable configuration.

Increased outdoor air or other heat sink (condenser heat rejection medium) temperatures have an opposite effect on the operation of the condenser. As the heat sink temperature increases, more condenser surface area is used for latent or isothermal heat transfer associated with condensing and a corresponding decrease in sensible heat transfer area used for subcooling. Therefore, increases in heat sink temperature result in decreased subcooling temperatures and increased condensing temperatures.

Referring to FIG. 6B, an increase in subcooling drives state 3 to the left, while an increase in condensing temperature shifts the curve connecting states 2 and 3 upward. High condensing temperatures can ultimately lead to compressor motor overload and increased compressor power consumption or lowered efficiency. As subcooling increases, heat is added to the evaporator, resulting in an upward shift of the curve connecting states 4 and 1. As the evaporating temperature increases, the specific volume of the refrigerant entering the compressor also increases, resulting in increased power input to the compressor. Therefore, increased levels of refrigerant charge and decreased chiller load conditions result in increased subcooling, which leads to increased compressor power input.

Superheat level is represented by the slight increase in temperature after the refrigerant leaves the saturation curve, as shown at state 1 in FIG. 6B. Vaporized refrigerant leaves the chiller's evaporator and enters the compressor as a superheated vapor. According to the present invention, the amount of superheat is not constant, and may vary based on operating conditions to achieve efficiency. In some systems, it is preferred that a minimum superheat be provided, e.g., 2.2 C, to avoid premature failure from droplet pitting and erosion, or liquid slugging. However, any amount of superheat generally represents an inefficiency. According to the present invention, the "cost" of low superheat levels may optionally be included in the optimization, in order to account for this factor. Otherwise, systems may be provided to reduce or control such problems, allowing low operating superheat levels.

Superheat level in the condenser may be increased, for example, by an accumulation of non-condensable gasses, which cause thermodynamic inefficiency. Therefore, according to one aspect of the invention, superheat level is monitored, and if it increases beyond a desired level, a non-condensable gas purge cycle, or other refrigerant purification, may be conducted. Non-condensable gases may be removed, for example, by extracting a gas phase from the condenser, and subjecting it to significant sub-cooling. The head-space of this sample will be principally non-condensing gasses, while refrigerant in the sample will liquefy. The liquefied refrigerant may be returned to the condenser or fed to the evaporator.

As discussed previously, an increase in heat sink temperature causes an increase in discharge pressure, which, in turn, causes the compressor's suction pressure to increase. The curves connecting states 2 and 3 and states 4 and 1 on FIG. 6B 3 both shift upward due to increases in heat sink temperature.

An upward shift in curves 4 through 1 or an increase in refrigerant evaporating temperature results in a decrease in the evaporating approach temperature. As the approach temperature decreases, the mass flow rate through the evaporator must increase in order to remove the proper amount of heat from the chilled water loop. Therefore, increasing heat sink temperatures cause evaporating pressure to increase, which leads to increased refrigerant mass flow rate through the evaporator. The combined effect of higher refrigerant mass flow rate through the evaporator and reduced approach temperature causes a decrease in superheat temperatures. Therefore, an inverse relationship exists between heat sink temperature and superheat temperatures.

With decreasing refrigerant charge, the curve connecting states 2 and 3 in FIG. 6B shifts downward and the subcooling level decreases or state 3 on the T-s diagram in FIG. 6B moves to the right. Bubbles begin to appear in the liquid line leading to the expansion device due to an increased amount of gaseous refrigerant leaving the condenser. Without the proper amount of subcooling in the refrigerant entering the expansion device (state 3 in FIG. 6B), the device does not operate optimally. In addition, a decrease in refrigerant charge causes a decrease in the amount of liquid refrigerant that flows into the evaporator and a subsequent decrease in capacity and increase in superheat and suction pressure. Thus, an inverse relationship exists between refrigerant charge level and superheat temperature.

According to the present invention, the discharge from the condenser includes a compliant reservoir, and thus may provide increased opportunity to achieve the desired level of subcooling. Likewise, because a reservoir is provided, the refrigerant charge is presumed to be in excess of that required under all operating circumstances, and therefore it will not be limiting. It is also possible to have a hybrid control strategy, wherein the reservoir is undersize, and therefore under light load, refrigerant accumulates in a reservoir, while under heavy load, the refrigerant charge is limiting. The control system according to the present invention may, of course, compensate for this factor in known manner. However, preferably, when the refrigerant charge is not limiting, the superheat temperature is independently controlled. Likewise, even where the refrigerant charge is sufficient, the evaporator may be artificially starved as a part of the control strategy.

Under extreme refrigerant undercharge conditions (below −20% charge), refrigerant undercharge causes an increase in suction pressure. In general, the average suction pressure increases with increasing refrigerant charge during all charge levels above −20%. Refrigerant charge level is a significant variable in determining both superheat temperature and suction pressure.

A system and method for measuring, analyzing and manipulating the capacity and efficiency of a refrigeration system by instrumenting the refrigeration system to measure efficiency, selecting a process variable for manipulation, and altering the process variable is provided. The process variable may be varied during operation of the refrigeration system while measuring efficiency thereof.

In an industrial process, a refrigeration system must have sufficient capacity to cool the target to a desired level. If the capacity is insufficient, the underlying process may fail, sometimes catastrophically. Thus, maintaining sufficient capacity, and often a margin of reserve, is a critical requirement. Therefore, it is understood that where capacity is limiting, deviations from optimal system operation may be tolerated or even desired in order to maintain the process within acceptable levels. Over the long term, steps to ensure that the system has adequate capacity for efficient operation may be taken. For example, system maintenance to reduce tube bundle scale or other heat transfer impediment, cleaning of refrigerant (e.g., to remove excess oil), and refrigerant-side heat transfer surfaces, and purging of non-condensable gases may be performed alone or in combination.

Efficiency is also important, although an inefficient system does not necessarily fail. Efficiency and system capacity are often related, since inefficiency typically reduces system capacity.

According to another embodiment of the invention, a set of state measurements are taken of the refrigeration system, which are then analyzed for self-consistency and to extract fundamental parameters, such as efficiency. Self-consistency, for example, assesses presumptions inherent in the system model, and therefore may indicate deviation of the actual system operation from the model operation. As the actual system deviates from the model, so too will the actual measurements of system parameters deviate from their thermodynamic theoretical counterparts. For example, as heat exchanger performance declines, due for example to scale accumulation on the tube bundle, or as compressor superheat temperature increases, for example due to non-condensable gases, these factors will be apparent in an adequate set of measurements of a state of the system. Such measurements may be used to estimate the capacity of the refrigeration system, as well as factors which lead to inefficiency of the system. These, in turn, can be used to estimate performance improvements which can be made to the system by returning it to an optimal state, and to perform a cost-benefit analysis in favor of any such efforts.

Typically, before extensive and expensive system maintenance is performed, it is preferable to instrument the system for real time performance monitoring, rather than simple state analysis. Such real time performance modeling is typically expensive, and not a part of normal system operation; whereas adequate information for a state analysis may be generally available from system controls. By employing a real time monitoring system, analysis of operational characteristics in a fluctuating environment may be assessed.

This scheme may also be used in other types of systems, and is not limited to refrigeration systems. Thus, a set of sensor measurements are obtained and analyzed with respect to system model. The analysis may then be used to tune system operational parameters, instigate a maintenance procedure, or as part of a cost-benefit analysis. Systems to which this method may be applied include, among others, internal combustion engines, turbomachinery, hydraulic and pneumatic systems.

Preferably, the efficiency is recorded in conjunction with the process variables. Thus, for each system, the actual sensitivity of efficiency, detected directly or by surrogate measures, to a process variable, may be measured.

According to a further aspect of the invention, a business method is provided for maintaining complex systems based on a cost-savings basis, rather than the typical cost of service or flat fee basis. According to this aspect of the invention, instead of servicing and maintaining a system for a fee based on a direct cost thereof, compensation is based on a system performance metric. For example, a baseline system performance is measured. Thereafter, a minimum system capacity is defined, and the system is otherwise serviced at the significant discretion of the service organization, presumably based on the cost-benefit of such service, with the service organization being compensated based on the system performance, for example a percentage of cost savings over the baseline. According to the present invention, data from the control system may be used to determine degradation of system parameters from an efficient state. The invention also allows monitoring of system performance, and communication of such performance data remotely to a service organization, such as through radio uplink, modem communication over telephone lines, or computer network. This communication may also permit immediate notification to the service organization of process shift, potentially in time to prevent subsequent and consequent system failure.

In this case, the system is performance monitored frequently or continuously, and if the system capacity is sufficient, decisions are made whether, at any time, it would be cost efficient to perform certain maintenance services, such as refrigerant purification, evaporator descaling or cleaning, purging of non-condensing gasses, or the like. Typically, if system capacity is substantially diminished below a prespecified reserve value (which may vary seasonally, or based on other factors), service is required. However, even in this case, degradation in system capacity may be due to a variety of factors, and the most efficient remediation may then be selected to cost-efficiently achieve adequate system performance.

After system service or maintenance, the control system may be initialized or retuned to ensure that pre-service or pre-maintenance parameters do not erroneously govern system operation.

According to a second main embodiment of the present invention, multivariate optimization and control may be conducted. In the case of multivariate analysis and control, interaction between variables or complex sets of time-constants may require a complex control system. A number of types of control may be implemented to optimize the operation of the system. Typically, after the appropriate type of control is selected, it must be tuned to the system, thus defining efficient operation and the relation of the input variables from sensors on the efficiency of the system. Often, controls often account for time delays inherent in the system, for example to avoid undesirable oscillation or instability. In many instances, simplifying presumptions, or segmentations are made in analyzing the operating space to provide traditional analytic solutions to the control problems. In other instances, non-linear techniques are employed to analyze the entire range of input variables. Finally, hybrid techniques are employed using both non-linear techniques and simplifying presumptions or segmentation of the operating space.

For example, in the second main embodiment of the invention, it is preferred that the range of operating conditions be segmented along orthogonal delineations, and the sensitivity of the system to process variable manipulation be measured for each respective variable within a segment. This, for example, permits a monotonic change in each variable during a testing or training phase, rather than requiring both increasing and decreasing respective variables in order to map the entire operating space. On the other hand, in the case of a single variable, it is preferred that the variable be altered continuously while measurements are taking place in order to provide a high speed of measurement.

Of course, it may not be possible to measure orthogonal (non-interactive) parameters. Therefore, another aspect of the invention provides a capability for receiving a variety of data relating to system operation and performance, and analyzing system performance based on this data. Likewise, during a continuous system performance monitoring, it may be possible to employ existing (normally occurring) system perturbations to determine system characteristics. Alternately, the system may be controlled to include a sufficient set of perturbations to determine the pertinent system performance parameters, in a manner which does not cause inefficient or undesirable system performance.

In an adaptive control system, the sensitivity of the operating efficiency to small perturbations in the control variables are measured during actual operation of the system, rather than in a testing or training mode, as in an autotuning system, which may be difficult to arrange and which may be inaccurate or incomplete if the system configuration or characteristics change after training or testing. Manual tuning, which requires an operator to run different test or trial and error procedures to determine the appropriate control parameters, is typically not feasible, since the characteristics of each installation over the entire operating range are not often fully characterized and are subject to change over time. Some manual tuning methods are described in D. E. Seborg, T. F. Edgar, and D. A. Mellichamp, Process Dynamics and Control, John Wiley & Sons, New York (1989) and A. B. Corripio, Tuning of Industrial Control Systems, Instrument Society of America, Research Triangle Park, N.C. (1990).

Autotuning methods require a periodically initiated tuning procedure, during which the controller will interrupt the normal process control to automatically determine the appropriate control parameters. The control parameters thus set will remain unchanged until the next tuning procedure. Some autotuning procedures are described in K. J. Astrom and T. Hagglund, Automatic Tuning of PID Controllers, Instrument Society of America, Research Triangle Park, N.C. (1988). Autotuning controllers may be operator or self initiated, either at fixed periods, based on an external event, or based on a calculated deviance from a desired system performance.

With adaptive control methods, the control parameters are automatically adjusted during normal operation to adapt to changes in process dynamics. Further, the control parameters are continuously updated to prevent the degraded performance which may occur between the tunings of the other methods. On the other hand, adaptive control methods may result in inefficiency due to the necessary periodic variance from an "optimal" condition in order to test the optimality. Further, adaptive controls may be complex and require a high degree of intelligence. Advantageously, the control may monitor system operation, and select or modify appropriate events for data acquisition. For example, in a system operating according to a pulse-width modulation paradigm, the pulse width and/or frequency may be varied in particular manner in order to obtain data about various operational states, without causing the system to unnecessarily deviate from acceptable operational ranges.

Numerous adaptive control methods have been developed. See, for example, C. J. Harris and S. A. Billings, Self-Tuning and Adaptive Control: Theory and Applications, Peter Peregrinus LTD (1981). There are three main approaches to adaptive control: model reference adaptive control ("MRAC"), self-tuning control, and pattern recognition adaptive control ("PRAC"). The first two approaches, MRAC and self-tuning, rely on system models which are generally quite complex. The complexity of the models is necessitated by the need to anticipate unusual or abnormal operating conditions. Specifically, MRAC involves adjusting the control parameters until the response of the system to a command signal follows the response of a reference model. Self-tuning control involves determining the parameters of a process model on-line and adjusting the control parameters based upon the parameters of the process model. Methods for performing MRAC and self-tuning control are described in K. J. Astrom and B. Wittenmark, Adaptive Control, Addison-Wesley Publishing Company (1989). In industrial chillers, adequate models of the system are typically unavailable for implementing the control, so that self-tuning controls are preferred over traditional MRAC. On the other hand, a sufficient model may be available for estimating system efficiency and capacity, as discussed above.

With PRAC, parameters that characterize the pattern of the closed-loop response are determined after significant setpoint changes or load disturbances. The control parameters are then adjusted based upon the characteristic parameters of the closed-loop response. A pattern recognition adaptive controller known as EXACT is described by T. W. Kraus and T. J. Myron, "Self-Tuning PID Controller uses Pattern Recognition Approach," Control Engineering, pp. 106-111, June 1984, E. H. Bristol and T. W. Kraus, "Life with Pattern Adaptation," Proceedings 1984 American Control Conference, pp. 888-892, San Diego, Calif. (1984), and K. J. Astrom and T. Hagglund, Automatic Tuning of PID Controllers, Instrument Society of America, Research Triangle Park, N.C. (1988). See also U.S. Pat. No. Re. 33,267, expressly incorporated herein by reference. The EXACT method, like other adaptive control methods, does not require operator intervention to adjust the control parameters under normal operation. Before normal operation may begin, EXACT requires a carefully supervised startup and testing period. During this period, an engineer determines the optimal initial values for controller gain, integral time, and derivative time. The engineer also determines the anticipated noise band and maximum wait time of the process. The noise band is a value representative of the expected amplitude of noise on the feedback signal. The maximum wait time is the maximum time the EXACT algorithm will wait for a second peak in the feedback signal after detecting a first peak. Further, before an EXACT-based controller is put into normal use, the operator may also specify other parameters, such as the maximum damping factor, the maximum overshoot, the parameter change limit, the derivative factor, and the step size. In fact, the provision of these parameters by an expert engineer is generally appropriate in the installation process for any control of an industrial chiller, and therefore such a manual definition of initial operating points is preferred over techniques which commence without a priori assumptions, since an unguided exploration of the operating space may be inefficient or dangerous.

According to the present invention, the system operational parameters need not be limited to an a priori "safe" operating range, where relatively extreme parameter values might provide improved performance, while maintaining a margin of safety, while detecting or predicting erroneous or artifact sensor data. Thus, using a model of the system constructed during operation, possibly along with manual input of probable normal operational limits, the system may analyze sensor data to determine a probability of system malfunction, and therefore with greater reliability adopt aggressive control strategies. If the probability exceeds a threshold, an error may be indicated or other remedial action taken.

A second known pattern recognition adaptive controller is described by Chuck Rohrer and Clay G. Nelser in "Self-Tuning Using a Pattern Recognition Approach," Johnson Controls, Inc., Research Brief 228 (Jun. 13, 1986). The Rohrer controller calculates the optimal control parameters based on a damping factor, which in turn is determined by the slopes of the feedback signal, and requires an engineer to enter a variety of initial values before normal operation may commence, such as the initial values for a proportional band, an integral time, a deadband, a tune noise band, a tune change factor, an input filter, and an output filter. This system thus emphasizes temporal control parameters.

Manual tuning of loops can take a long time, especially for processes with slow dynamics, including industrial and commercial chillers. Different methods for autotuning PID controllers are described by Astrom, K. J., and T. Hagglund, Automatic Tuning of PID Controllers, Instrument Society of American, Research Triangle Park, N.C., 1988, and Seborg, D. E. T., T. F. Edgar, and D. A. Mellichamp, Process Dynamics and Control, John Wiley & sons, 1989. Several methods are based on the open loop transient response to a step change in controller output and other methods are based on the frequency response while under some form of feedback control. Open loop step response methods are sensitive to load disturbances, and frequency response methods require a large amount of time to tune systems with long time constants. The Ziegler-Nichols transient response method characterizes the response to a step change in controller output, however, implementation of this method is sensitive to noise. See also, Nishikawa, Yoshikazu, Nobuo Sannomiya, Tokuji Ohta, and Haruki Tanaka, "A Method for Autotuning of PID Control Parameters," Automatica, Volume 20, No. 3, 1984.

For some systems, it is often difficult to determine if a process has reached a steady-state. In many systems, if the test is stopped too early, the time delay and time constant estimates may be significantly different than the actual values. For example, if a test is stopped after three time constants of the first order response, then the estimated time constant equals 78% of the actual time constant, and if the test is stopped after two time constants, then the estimated time constant equals 60% of the actual time constant. Thus, it is important to analyze the system in such a way as to accurately determine time-constants. Thus, in a self-tuning system, the algorithm may obtain tuning data from normal perturbations of the system, or by periodically testing the sensitivity of the plant to modest perturbations about the operating point of the controlled variable(s). If the system determines that the operating point is inefficient, the controlled variable(s) are altered in order to improve efficiency toward an optimal operating point. The efficiency may be determined on an absolute basis, such as by measuring kWatt hours consumed (or other energy consumption metric) per BTU of cooling, or through surrogate measurements of energy consumption or cooling, such as temperature differentials and flow data of refrigerant near the compressor and/or water in the secondary loop near the evaporator/heat exchanger. Where cost per BTU is not constant, either because there are different sources available, or the cost varies over time, efficiency may be measured in economic terms and optimized accordingly. Likewise, the efficiency calculation may be modified by including other relevant "costs".

A full power management system (PMS) is not required in order to optimize the efficiency. However, this PMS may be provided depending on cost and availability, or other considerations.

In many instances, parameters will vary linearly with load and be independent of other variables, thus simplifying analysis and permitting traditional (e.g., linear, proportional-integral-differential (PID)) control design. See, U.S. Pat. Nos. 5,568,377, 5,506,768, and 5,355,305, expressly incorporated herein by reference. On the other hand, parameters which have multifactorial dependencies are not easily resolved. In this case, it may be preferable to segment the control system into linked invariant multifactorial control loops, and time-varying simple control loops, which together efficiently control the entire system, as in the preferred embodiment of the invention.

Alternately, a neural network or fuzzy-neural network control may be employed. In order to train a neural network, a number of options are available. One option is to provide a specific training mode, in which the operating conditions are varied, generally methodically, over the entire operating space, by imposing artificial or controlled loads and extrinsic parameters on the system, with predefined desired system responses, to provide a training set. Thereafter, the neural network is trained, for example by back propagation of errors, to produce an output that moves the system toward an optimal operating point for the actual load conditions. The controlled variables may be, for example, oil concentration in the refrigerant and/or refrigerant charge. See, U.S. Pat. No. 5,579,993, expressly incorporated herein by reference.

Another option is to operate the system in a continual learning mode in which the local operating space of the system is mapped by the control during operation, in order to determine a sensitivity of the system to perturbations in process variables, such as process load, ambient temperature, oil concentration in the refrigerant and/or refrigerant charge. When the system determines that the present operating point is suboptimal, it alters the operating point toward a presumable more efficient condition. The system may also broadcast an alert that specific changes are recommended to return the system to a more efficient operating mode, where such changes are not controlled by the system itself. If the process has insufficient variability to adequately map the operating point, the control algorithm may conduct a methodical search of the space or inject a pseudorandom signal into one or more controlled variables seeking to detect the effect on the output (efficiency). Generally, such search techniques will themselves have only a small effect on system efficiency, and will allow the system to learn new conditions, without explicitly entering a learning mode after each alteration in the system.

Preferably, the control builds a map or model of the operating space from experience, and, when the actual system performance corresponds to the map or model, uses this map or model to predict an optimal operating point and directly control the system to achieve the predicted most-efficient state. On the other hand, when the actual performance does not correspond to the map or model, the control seeks to generate a new map or model. It is noted that such a map or model may itself have little physical significance, and thus is generally useful only for application within the specific network which created it. See, U.S. Pat. No. 5,506,768, expressly incorporated herein by reference. It may also be possible to constrain the network to have weights which correspond to physical parameters, although this constraint may lead to either control errors or inefficient implementation and realization.

See, also:

A. B. Corripio, "Tuning of Industrial Control Systems", Instrument Society of America, Research Triangle Park, N.C. (1990) pp. 65-81.

C. J. Harris & S. A. Billings, "Self-Tuning and Adaptive Control: Theory and Applications", Peter Peregrinus LTD (1981) pp. 20-33.

C. Rohrer & Clay Nesler, "Self-Tuning Using a Pattern Recognition Approach", Johnson Controls, Inc., Research Brief 228 (Jun. 13, 1986).

D. E. Seborg, T. F. Edgar, & D. A. Mellichamp, "Process Dynamics and Control", John Wiley & Sons, N.Y. (1989) pp. 294-307, 538-541.

E. H. Bristol & T. W. Kraus, "Life with Pattern Adaptation", Proceedings 1984 American Control Conference, pp. 888-892, San Diego, Calif. (1984).

Francis Schied, "Shaum's Outline Series-Theory & Problems of Numerical Analysis", McGraw-Hill Book Co., NY (1968) pp. 236, 237, 243, 244, 261.

K. J. Astrom and B. Wittenmark, "Adaptive Control", Addison-Wesley Publishing Company (1989) pp. 105-215.

K. J. Astrom, T. Hagglund, "Automatic Tuning of PID Controllers", Instrument Society of America, Research Triangle Park, N.C. (1988) pp. 105-132.

R. W. Haines, "HVAC Systems Design Handbook", TAB Professional and Reference Books, Blue Ridge Summit, Pa. (1988) pp. 170-177.

S. M. Pandit & S. M. Wu, "Timer Series & System Analysis with Applications", John Wiley & Sons, Inc., NY (1983) pp. 200-205.

T. W. Kraus 7 T. J. Myron, "Self-Tuning PID Controller Uses Pattern Recognition Approach", Control Engineering, pp. 106-111, June 1984.

G F Page, J B Gomm & D Williams: "Application of Neural Networks to Modelling and Control", Chapman & Hall, London, 1993.

Gene F Franklin, J David Powell & Abbas Emami-Naeini: "Feedback Control of Dynamic Systems", Addison-Wesley Publishing Co. Reading, 1994.

George E P Box & Gwilym M Jenkins: "Time Series Analysis: Forecasting and Control", Holden Day, San Francisco, 1976.

Sheldon G Lloyd & Gerald D Anderson: "Industrial Process Control", Fisher Controls Co., Marshalltown, 1971.

Kortegaard, B. L., "PAC-MAN, a Precision Alignment Control System for Multiple Laser Beams Self-Adaptive Through the Use of Noise", Los Alamos National Laboratory, date unknown.

Kortegaard, B. L., "Superfine Laser Position Control Using Statistically Enhanced Resolution in Real Time", Los Alamos National Laboratory, SPIE-Los Angeles Technical Symposium, Jan. 23-25, 1985.

Donald Specht, IEEE Transactions on Neural Networks, "A General Regression Neural Network", November 1991, Vol. 2, No. 6, pp. 568-576.

Fuzzy controllers may be trained in much the same way neural networks are trained, using backpropagation techniques, orthogonal least squares, table look-up schemes, and nearest neighborhood clustering. See Wang, L., Adaptive fuzzy systems and control, New Jersey: Prentice-Hall (1994); Fu-Chuang Chen, "Back-Propagation Neural Networks for Nonlinear Self-Tuning Adaptive Control", 1990 IEEE Control System Magazine.

Thus, while a system model may be useful, especially for large changes in system operating parameters, the adaptation mechanism is advantageous in that it does not rely on an explicit system model, unlike many of the on-line adaptation mechanisms such as those based on Lyapunov methods. See Wang, 1994; Kang, H. and Vachtsevanos, G., "Adaptive fuzzy logic control," IEEE International Conference on Fuzzy Systems, San Diego, Calif. (March 1992); Layne, J., Passino, K. and Yurkovich, S., "Fuzzy learning control for antiskid braking systems," IEEE Transactions on Control Systems Technology 1 (2), pp. 122-129 (1993).

The adaptive fuzzy controller (AFC) is a nonlinear, multiple-input multiple-output (MIMO) controller that couples a fuzzy control algorithm with an adaptation mechanism to continuously improve system performance. The adaptation mechanism modifies the location of the output membership functions in response to the performance of the system. The adaptation mechanism can be used off-line, on-line, or a combination of both. The AFC can be used as a feedback controller, which acts using measured process outputs and a reference trajectory, or as a feedback controller with feedforward compensation, which acts using not only measured process outputs and a reference trajectory but also measured disturbances and other system parameters. See, U.S. Pat. Nos. 5,822,740, 5,740,324, expressly incorporated herein by reference.

As discussed above, a significant process variable is the oil content of the refrigerant in the evaporator. This variable may, in fact, be slowly controlled, typically by removal only, since only on rare occasions will the oil content be lower than desired for any significant length of time, and removing added oil is itself inefficient. To define the control algorithm, the process variable, e.g., oil content, is continuously varied by partially distilling the refrigerant at, or entering, the evaporator, to remove oil, providing clean refrigerant to the evaporator in an auto-tuning procedure. Over time, the oil content will approach zero. The system performance is monitored during this process. Through this method, the optimal oil content in the evaporator and the sensitivity to changes in oil content can be determined. In a typical installation, the optimum oil concentration in the evaporator is near 0%, while when the system is retrofitted with a control system for controlling the oil content of the evaporator, it is well above optimum. Therefore, the auto-tuning of the control may occur simultaneously with the remediation of the inefficiency.

In fact, the oil content of the evaporator may be independently controlled, or controlled in concert with other variables, such as refrigerant charge (or effective charge, in the case of the preferred embodiment which provides an accumulator to buffer excess refrigerant and a control loop to regulate level of refrigerant in the evaporator).

According to one design, an external reservoir of refrigerant is provided. Refrigerant is withdrawn from the evaporator through a partial distillation apparatus into the reservoir, with the oil separately stored. Based on the control optimization, refrigerant and oil are separately returned to the system, i.e., refrigerant vapor to the evaporator and oil to the compressor loop. In this way, the optimum oil concentration may be maintained for respective refrigerant charge levels. It is noted that this system is generally asymmetric; withdrawal and partial distillation of refrigerant is relatively slow, while charging the system with refrigerant and oil are relatively quick. If rapid withdrawal of refrigerant is desired, the partial distillation system may be temporarily bypassed. However, typically it is more important to meet peak loads quickly than to obtain most efficient operating parameters subsequent to peak loads.

It is noted that, according to the second embodiment of the present invention, both refrigerant-to-oil ratio and refrigerant fill may be independently controlled variables of system operation.

The compressor may also be modulated, for example by controlling a compression ratio, compressor speed, compressor duty cycle (pulse frequency, pulse width and/or hybrid modulation), compressor inlet flow restriction, or the like.

While the immediate efficiency of the evaporator may be measured assuming a single compartment within the evaporator, and therefore short time delay for mixing, it is also noted that an oil phase may adhere to the evaporator tube walls. By flowing clean refrigerant through the evaporator, this oil phase, which has a longer time-constant for release from the walls than a mixing process of the bulk refrigerant, is removed. Advantageously, by modeling the evaporator and monitoring system performance, by removing the oil phase from the refrigerant side of the evaporator tub walls, a scale or other deposit on the water-side of the tube wall may be estimated. This, it turns out, is a useful method for determining an effect on efficiency of such deposits, and may allow an intelligent decision as to when an expensive and time consuming descaling of the tube bundles is required Likewise, by removing the excess oil film from the tube wall, efficiency may be maintained, delaying the need for descaling.

The optimal refrigerant charge level may be subject to variation with nominal chiller load and plant temperature, while related (dependent) variables include efficiency (kW/ton), superheat temperature, subcooling temperature, discharge pressure, superheat temperature, suction pressure and chilled water supply temperature percent error. Direct efficiency measurement of kilowatt-hours per ton may be performed, or inferred from other variables, preferably process temperatures and flow rates.

Complex interdependencies of the variables, as well as the preferred use of surrogate variables instead of direct efficiency data, weigh in favor of a non-linear neural network model, for example similar to the model employed in Bailey, Margaret B., "System Performance Characteristics of a Helical Rotary Screw Air-Cooled Chiller Operating Over a Range of Refrigerant Charge Conditions", ASHRAE Trans. 1998 104(2). In this case, the model has an input layer, two hidden layers, and an output layer. The output layer typically has one node for each controlled variable, while the input layer contains one node for each signal. The Bailey neural network includes five nodes in the first hidden layer and two nodes for each output node in the second hidden layer. Preferably, the sensor data is processed prior to input into the neural network model. For example, linear processing of sensor outputs, data normalization, statistical processing, etc. may be performed to reduce noise, provide appropriate data sets, or to reduce the topological or computational complexity of the neural network. Fault detection may also be integrated in the system, either by way of further elements of the neural network (or a separate neural network) or by analysis of the sensor data by other means.

Feedback optimization control strategies are may be applied to transient and dynamic situations. Evolutionary optimization or genetic algorithms, which intentionally introduce small perturbations of the independent control variable, to compare the result to an objective function, may be made directly upon the process itself. In fact, the entire theory of genetic algorithms may be applied to the optimization of refrigeration systems. See, e.g., U.S. Pat. Nos. 6,496,761; 6,493,686; 6,492,905; 6,463,371; 6,446,055; 6,418,356; 6,415,272; 6,411,944; 6,408,227; 6,405,548; 6,405,122; 6,397,113; 6,349,293; 6,336,050; 6,324,530; 6,324,529; 6,314,412; 6,304,862; 6,301,910; 6,300,872; 6,278,986; 6,278,962; 6,272,479; 6,260,362; 6,250,560; 6,246,972; 6,230,497; 6,216,083; 6,212,466; 6,186,397; 6,181,984; 6,151,548; 6,110,214; 6,064,996; 6,055,820; 6,032,139; 6,021,369; 5,963,929; 5,921,099; 5,946,673; 5,912,821; 5,877,954; 5,848,402; 5,778,688; 5,775,124; 5,774,761; 5,745,361; 5,729,623; 5,727,130; 5,727,127; 5,649,065; 5,581,657; 5,524,175; 5,511,158, each of which is expressly incorporated herein by reference.

According to the present invention, the control may operate on multiple independent or interdependent parameters. Steady state optimization may be used on complex processes exhibiting long time constants and with disturbance variables that change infrequently. Hybrid strategies are also employed in situations involving both long-term and short-term dynamics. The hybrid algorithms are generally more complex and require custom tailoring for a truly effective implementation. Feedback control can sometimes be employed in certain situations to achieve optimal plant performance.

According to one embodiment of the invention, a refrigerant-side vs. water side heat transfer impairment in an evaporator heat exchanger may be distinguished by selectively modifying a refrigerant composition, for example to remove oil and other impurities. For example, as the oil level of the refrigerant is reduced, oil deposits on the refrigerant side of the heat exchanger tubes will also be reduced, since the oil deposit is generally soluble in the pure refrigerant. The heat exchanger may then be analyzed in at least two different ways. First, if the refrigerant-side is completely cleaned of deposits, then any remaining diminution of system performance must be due to deposits on the water side. Second, assuming a linear process of removing impairment on the refrigerant side, the amount of refrigerant-side impairment may be estimated without actually removing the entire impairment. While, as stated above, a certain amount of oil may result in more efficient operation than pure refrigerant, this may be added back, if necessary. Since this process of purifying the refrigerant is relatively simpler and less costly than descaling the evaporator to remove water-side heat exchange impairment, and is of independent benefit to system operation, it therefore provides an efficient procedure to determining the need for system maintenance. On the other hand, refrigerant purification consumes energy, and may reduce capacity, and results in very low, possibly suboptimal, oil concentrations in the evaporator, so continuous purification is generally not employed.

Thus, it is seen that a perturbation in system response in order to determine a parameter of the system is not limited to compressor control, and, for example, changes in refrigerant purity, refrigerant charge, oil level, and the like, may be made in order to explore system operation.

Multivariate processes in which there are numerous interactive effects of independent variables upon the process performance can best be optimized by the use of feedforward control. However, an adequate predictive mathematical model of the process is required. This, for example, may be particularly applicable to the inner compressor control loop. Note that the on-line control computer will evaluate the consequences of variable changes using the model rather than perturbing the process itself. Such a predictive mathematical model is therefore of particular use in its failure, which is indicative of system deviation from a nominal operating state, and possibly indicative of required system maintenance to restore system operation.

To produce a viable optimization result, the mathematical model in a feedforward technique must be an accurate representation of the process. To ensure a one-to-one correspondence with the process, the model is preferably updated just prior to each use. Model updating is a specialized form of feedback in which model predictions are compared with the current plant operating status. Any variances noted are then used to adjust certain key coefficients in the model to enforce the required agreement. Typically, such models are based on physical process elements, and therefore may be used to imply real and measurable characteristics.

In chillers, many of the relevant timeconstants are very long. While this reduces short latency processing demands of a real time controller, it also makes corrections slow to implement, and poses the risk of error, instability or oscillation if the timeconstants are erroneously computed. Further, in order to provide a neural network with direct temporal control sensitivity, a large number of input nodes may be required to represent the data trends. Preferably, temporal calculations are therefore made by linear computational method, with transformed time-varying data input to the neural network. The transform may be, for example, in the time-frequency representation, or time-wavelet representation. For example, first and second derivatives (or higher order, as may be appropriate) of sensor data or transformed sensor data may be calculated and fed to the network. Alternately or additionally, the output of the neural network may be subjected to processing to generate appropriate process control signals. It is noted that, for example, if the refrigerant charge in a chiller is varied, it is likely that critical timeconstants of the system will also vary. Thus, a model which presumes that the system has a set of invariant timeconstants may produce errors, and the preferred system according to the present invention makes no such critical presumptions. The control system therefore preferably employs flexible models to account for the interrelation of variables.

Other potentially useful process parameters to measure include moisture, refrigerant breakdown products, lubricant breakdown products, non-condensable gasses, and other known impurities in the refrigerant. Likewise, there are also mechanical parameters which may have optimizable values, such as mineral deposits in the brine tubes (a small amount of mineral deposits may increase turbulence and therefore reduce a surface boundary layer), and air or water flow parameters for cooling the condenser.

Typically, there are a set of process parameters which theoretically have an optimum value of 0, while in practice, achieving this value is difficult or impossible to obtain or maintain. This difficulty may be expressed as a service cost or an energy cost, but in any case, the control system may be set to allow theoretically suboptimal parameter readings, which are practically acceptable and preferable to remediation. A direct cost-benefit analysis may be implemented. However, at some threshold, remediation is generally deemed efficient. The control system may therefore monitor these parameters and either indicate an alarm, implement a control strategy, or otherwise act. The threshold may, in fact, be adaptive or responsive to other system conditions; for example, a remediation process would preferably be deferred during peak load periods if the remediation itself would adversely affect system performance, and sufficient reserve capacity exists to continue operation.

Thus, it is seen that in some instances, as exemplified by oil levels in the evaporator, an initial (or periodic) determination of system sensitivity to the sensed parameter is preferred, while in other instances, an adaptive control algorithm is preferred.

In the case of autotuning processes, after the optimization calculations are complete, the process variable, e.g., the oil content of the evaporator, may be restored to the optimal level. It is noted that the process variable may change over time, e.g., the oil level in the evaporator will increase, so it is desired to select an initial condition which will provide the maximum effective efficiency between the initial optimization and a subsequent maintenance to restore the system to efficient operation. Therefore, the optimization preferably determines an optimum operating zone, and the process variable established at the lower end of the zone after measurement. This lower end may be zero, but need not be, and may vary for each system measured.

In this way, it is not necessary to continuously control the process variable, and rather the implemented control algorithm may, for example, include a wide deadband and manual implementation of the control process.

A monitor may be provided for the process variable, to determine when reoptimization is necessary. During reoptimzation, it is not always necessary to conduct further efficiency measurements; rather, the prior measurements may be used to redefine the desired operating regime.

Thus, after the measurements are taken to a limit (e.g., near zero oil or beyond the expected operating regime), the system is restored, if necessary, to achieve a desired initial efficiency, allowing for gradual variations, e.g., accumulation of oil in the evaporator, while still maintaining appropriate operation for a suitable period.

An efficiency measurement, or surrogate measurement(s) (e.g., compressor amperage, thermodynamic parameters) may subsequently be employed to determine when process variable, e.g., the oil level, has change or accumulated to sufficient levels to require remediation. Alternately, a direct oil concentration measurement may be taken of the refrigerant in the evaporator. In the case of refrigeration compressor oil, for example, the monitor may be an optical sensor, such as disclosed in U.S. Pat. No. 5,694,210, expressly incorporated herein by reference.

A closed loop feedback device may seek to maintain a process variable within a desired range. Thus, a direct oil concentration gage, typically a refractometer, measures the oil content of the refrigerant. A setpoint control, proportional, differential, integral control, fuzzy logic control or the like is used to control a bypass valve to a refrigerant distillation device, which is typically oversize, and operating well within its control limits. As the oil level increases to a level at which efficiency is impaired, the refrigerant is distilled to remove oil. The oil is, for example, returned to the compressor lubrication system, while the refrigerant is returned to the compressor inlet. In this manner, closed loop feedback control may be employed to maintain the system at optimum efficiency. It is noted that it is also possible to employ an active in-line distillation process which does not bypass the evaporator. For example, the Zugibeast® system (Hudson Technologies, Inc.) may be employed, however, this is system typically larger and more complex than necessary for this purpose. U.S. Pat. No. 5,377,499, expressly incorporated herein by reference, thus provides a portable device for refrigerant reclamation. In this system, refrigerant may be purified on site, rather than requiring, in each instance, transporting of the refrigerant to a recycling facility. U.S. Pat. No. 5,709,091, expressly incorporated herein by reference, also discloses a refrigerant recycling method and apparatus.

In the oil separating device, advantageously, the refrigerant is fed into a fractional distillation chamber controlled to be at a temperature below its boiling point, and therefore condenses into a bulk of liquid refrigerant remaining within the vessel. Relatively pure refrigerant is present in the gas phase, while less volatile impurities remain in the liquid phase. The pure refrigerant is used to establish the chamber temperature, thus providing a sensitive and stable system. The fractionally distilled purified liquid refrigerant is available from one port, while impurities are removed through another port. The purification process may be manual or automated, continuous or batch.

One aspect of the invention derives from a relatively new understanding that the optimum oil level in the evaporator of a refrigeration system may vary by manufacturer, model and particular system, and that these variables are significant in the efficiency of the process and may change over time. The optimal oil level need not be zero, for example in fin tube evaporators, the optimal oil level may be between 1-5%, at which the oil bubbles and forms a film on the tube surfaces, increasing heat transfer coefficient. On the other hand, so-called nucleation boiling heat transfer tubes have a substantially lower optimal oil concentration, typically less than about 1%.

Seeking to maintain a 0% oil concentration may itself be inefficient, since the oil removal process may require expenditure of energy and bypass of refrigerant, and an operating system has a low but continual level of leakage. Further, the oil level in the condenser may also impact system efficiency, in a manner inconsistent with the changes in efficiency of the evaporator.

Thus, this aspect of the invention does not presume an optimum level of a particular process variable parameter. Rather, a method according to the invention explores the optimum value, and thereafter allows the system to be set near the optimum Likewise, the method permits periodic "tune-ups" of the system, rather than requiring continuous tight maintenance of a control parameter, although the invention also provides a system and method for achieving continuous monitoring and/or control.

The refrigeration systems or chillers may be large industrial devices, for example 3500 ton devices which draw 4160V at 500 A max (2 MW). Therefore, even small changes in efficiency may produce substantial savings in energy costs. Possibly more importantly, when efficiency drops, it is possible that the chiller is unable to maintain the process parameter within the desired range. During extended operation, for example, it is possible for the oil concentration in the evaporator to increase above 10%, and the overall capacity of the system to drop below 1500 tons. This can result in process deviations or failure, which may require immediate or expensive remediation. Proper maintenance, to achieve a high optimum efficiency, may be quite cost effective.

BRIEF DESCRIPTION OF THE DRAWINGS

The invention will now be described with reference to the accompanying drawings, in which.

DETAILED DESCRIPTION OF THE PREFERRED EMBODIMENTS

The foregoing and other objects, features and advantages of the present invention will become more readily apparent to those skilled in the art to which the invention pertains upon reference to the following detailed description of one of the best modes for carrying out the invention, when considered in conjunction with the accompanying drawing in which preferred embodiments of the invention are shown and described by way of illustration, and not of limitation, wherein:

Example 1

Figure 1:
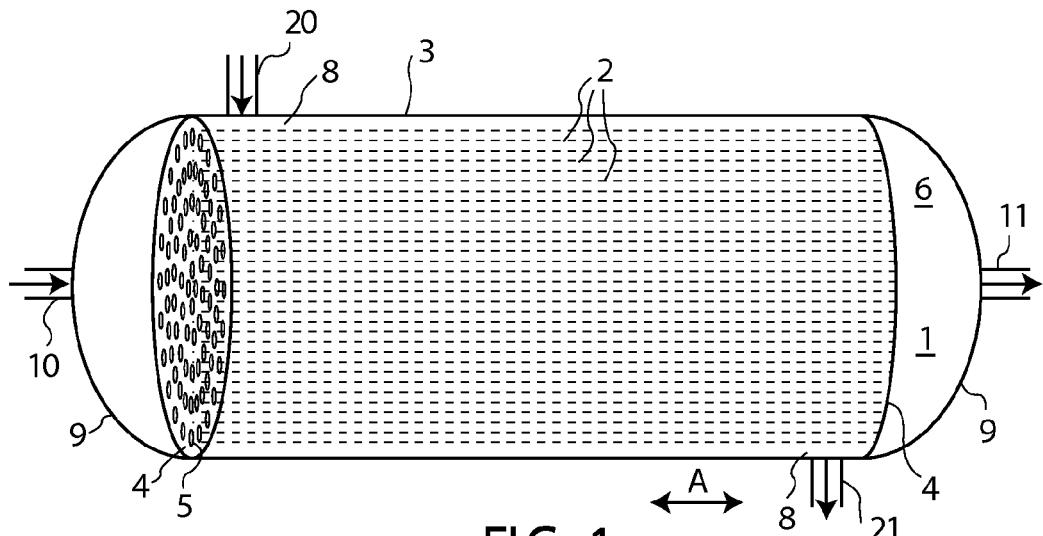
FIG. 1 is a schematic view of a known tube in shell heat exchanger evaporator.
Figure 2:
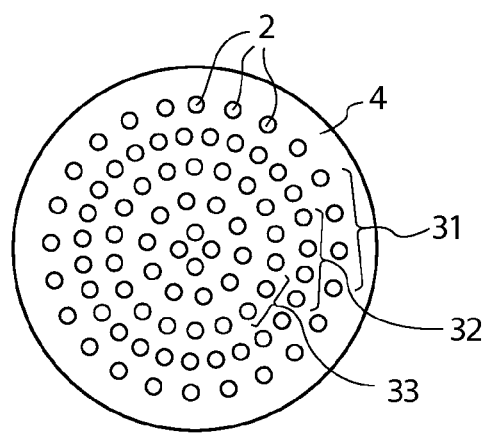
FIG. 2 shows an end view of a tube plate, showing the radially symmetric arrangement of tubes of a tube bundle, each tube extending axially along the length of the heat exchanger evaporator.

As shown in FIGS. 1-2, a typical tube in shell heat exchanger 1 consists of a set of parallel tubes 2 extending through a generally cylindrical shell 3. The tubes 2 are held in position with a tube plate 4, one of which is provided at each end 5 of the tubes 2. The tube plate 4 separates a first space 6, continuous with the interior of the tubes 7, from a second space 8, continuous with the exterior of the tubes 2. Typically, a domed flow distributor 9 is provided at each end of the shell 3, beyond the tube sheet 4, for distributing flow of the first medium from a conduit 10 through the tubes 2, and thence back to a conduit 11. In the case of volatile refrigerant, the system need not be symmetric, as the flow volumes and rates will differ at each side of the system. Not shown are optional baffles or other means for ensuring optimized flow distribution patterns in the heat exchange tubes.

Figure 3:
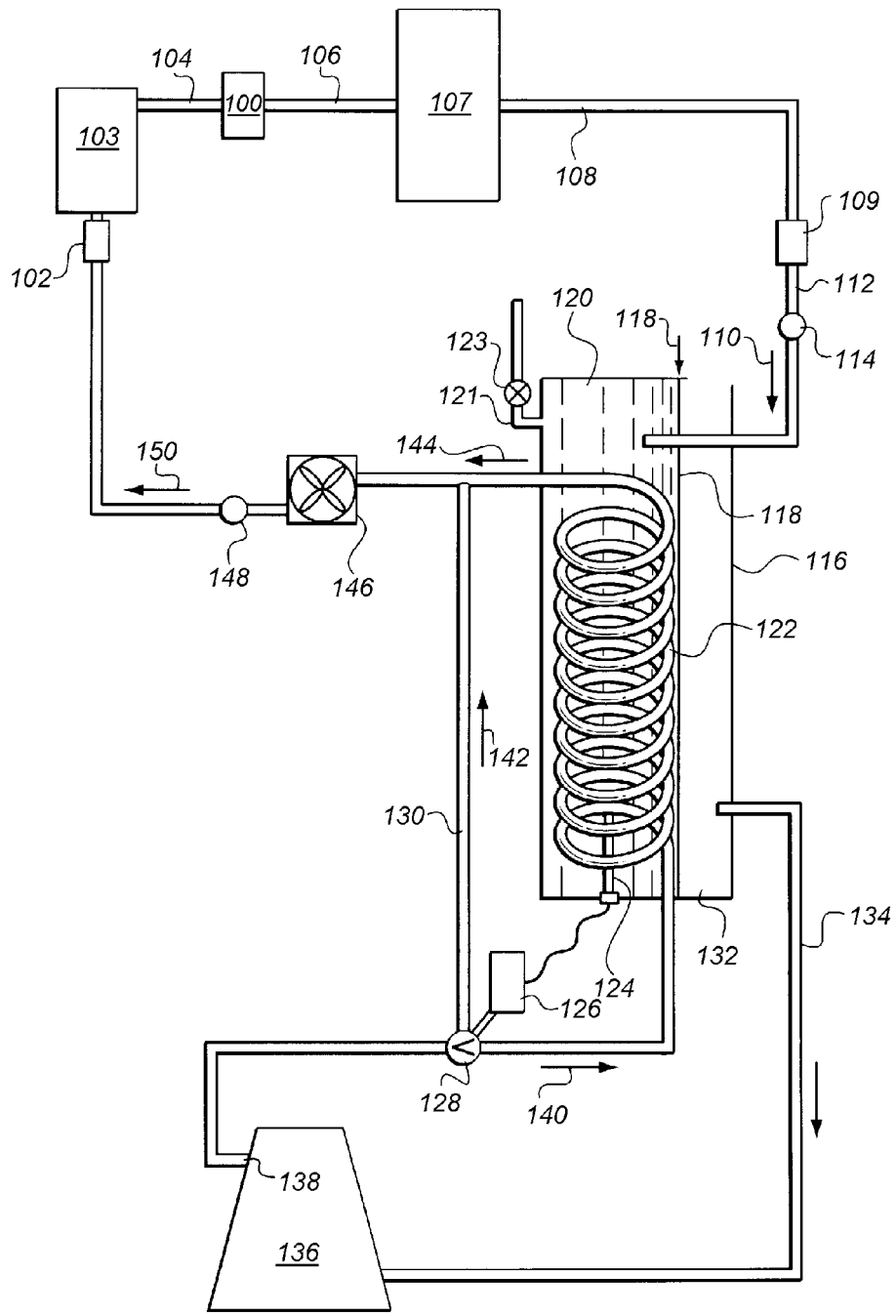
FIG. 3 shows a schematic drawing of a partial distillation system for removing oil from a refrigerant flow stream.

As shown in FIG. 3, a refrigerant cleansing system provides an inlet 112 for receiving refrigerant from the condenser, a purification system employing a controlled distillation process, and an outlet 150 for returning purified refrigerant. This portion of the system is similar to the system described in U.S. Pat. No. 5,377,499, expressly incorporated herein by reference.

The compressor 100 compresses the refrigerant, while condenser 107, sheds the heat in the gas. A small amount of compressor oil is carried with the hot gas to the condenser 107, where it cools and condenses into a mixed liquid with the refrigerant, and exits through line 108 and fitting 14. Isolation valves 102, 109 are provided to selectively allow insertion of a partial distillation apparatus 105 within the refrigerant flow path. The refrigerant from the partial distillation apparatus 105 is received by the evaporator 103 through the isolation valve 102.

The partial distillation apparatus 105 is capable of boiling contaminated refrigerant in a distillation chamber 130, with the distillation is controlled by throttling the refrigerant vapor. Contaminated refrigerant liquid 120 is fed, represented by directional arrow 110, through an inlet 112 and a pressure regulating valve 114, into distillation chamber 116, to establish liquid level 118. A contaminated liquid drain 121 is also provided, with valve 123. A high surface area conduit, such as a helical coil 122, is immersed beneath the level 118 of contaminated refrigerant liquid. Thermocouple 124 is placed at or near the center of coil 122 for measuring distillation temperature for purposes of temperature control unit 126, which controls the position of three-way valve 128, to establish as fractional distillation temperature. Temperature control valve 128 operates, with bypass conduit 130, so that, as vapor is collected in the portion 132 of distillation chamber 116 above liquid level 118, it will feed through conduit 134 to compressor 136, to create a hot gas discharge at the output 138 of compressor 136, which are fed through three-way valve 128, under the control of temperature control 126. In those situations where thermocouple 124 indicates a fractional distillation temperature above threshold, bypass conduit 130 receives some of the output from compressor 136; below threshold, the output will flow as indicated by arrow 140 into helical coil 122; near threshold, gases from the compressor output are allowed to flow partially along the bypass conduit and partially into the helical coil to maintain that temperature. Flow through bypass conduit 130 and from helical coil 122, in directions 142, 144, respectively, will pass through auxiliary condenser 146 and pressure regulating valve 148 to produce a distilled refrigerant outlet indicated by directional arrow 150. Alternatively, condenser 146 is controlled by an additional temperature control unit, controlled by the condenser output temperature. Thus, oil from the condenser 107 is removed before entering the evaporator 105. By running the system over time, oil accumulation in the evaporator 103 will drop, thus cleansing the system.

Figure 4:
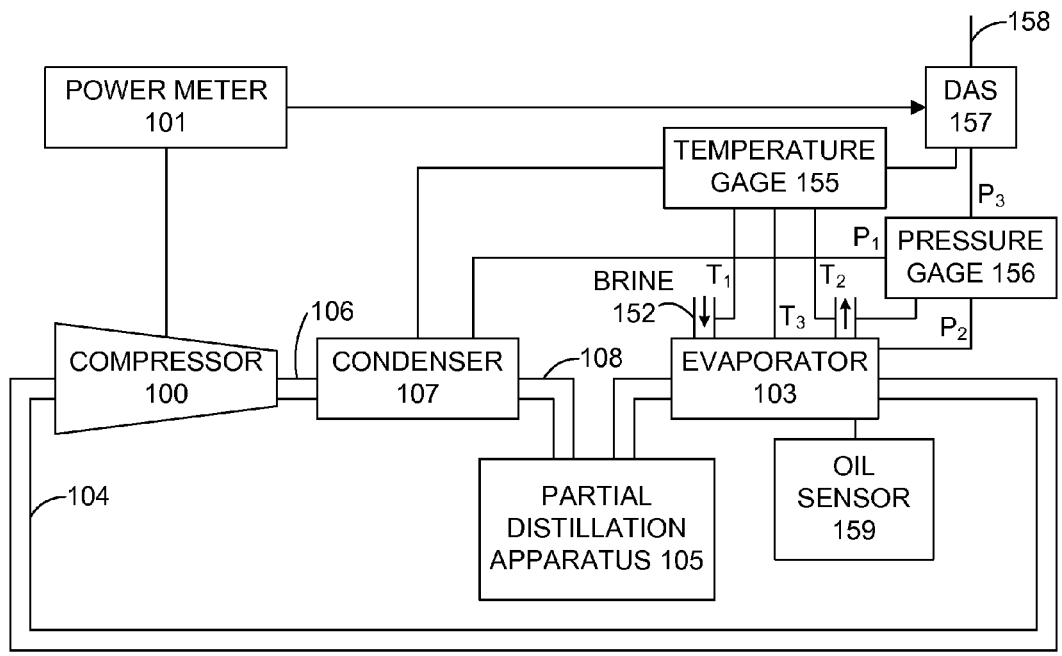
FIG. 4 shows a schematic of a chiller efficiency measurement system.

FIG. 4 shows an instrumented chiller system, allowing periodic or batch reoptimization, or allowing continuous closed loop feedback control of operating parameters. Compressor 100 is connected to a power meter 101, which accurately measures power consumption by measuring Volts and Amps drawn. The compressor 100 produces hot dense refrigerant vapor in line 106, which is fed to condenser 107, where latent heat of vaporization and the heat added by the compressor 100 is shed. The refrigerant carries a small amount of compressor lubricant oil. The condenser 107 is subjected to measurements of temperature and pressure by temperature gage 155 and pressure gage 156. The liquefied, cooled refrigerant, including a portion of mixed oil, if fed through line 108 to an optional partial distillation apparatus 105, and hence to evaporator 103. In the absence of the partial distillation apparatus 105, the oil from the condenser 107 accumulates in the evaporator 103. The evaporator 103 is subjected to measurements of refrigerant temperature and pressure by temperature gage 155 and pressure gage 156. The chilled water in inlet line 152 and outlet line 154 of the evaporator 103 are also subject to temperature and pressure measurement by temperature gage 155 and pressure gage 156. The evaporated refrigerant from the evaporator 103 returns to the compressor through line 104.

The power meter 101, temperature gage 155 and pressure gage 156 each provide data to a data acquisition system 157, which produces output 158 representative of an efficiency of the chiller, in, for example, BTU/kWH. An oil sensor 159 provides a continuous measurement of oil concentration in the evaporator 103, and may be used to control the partial distillation apparatus 105 or determine the need for intermittent reoptimization, based on an optimum operating regime. The power meter 101 or the data acquisition system 157 may provide surrogate measurements to estimate oil level in the evaporator or otherwise a need for oil removal.

Figure 5:
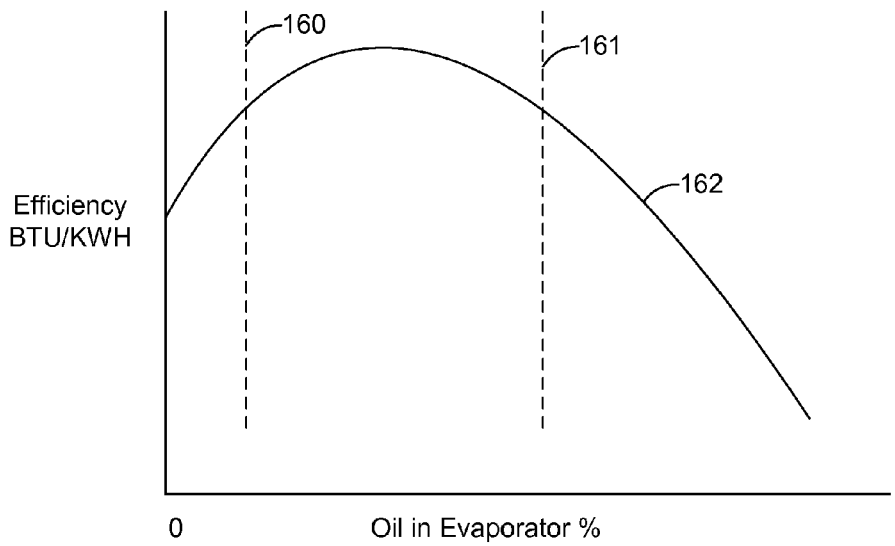
FIG. 5 shows a stylized representative efficiency graph with respect to changes in evaporator oil concentration.
Figure 6A:
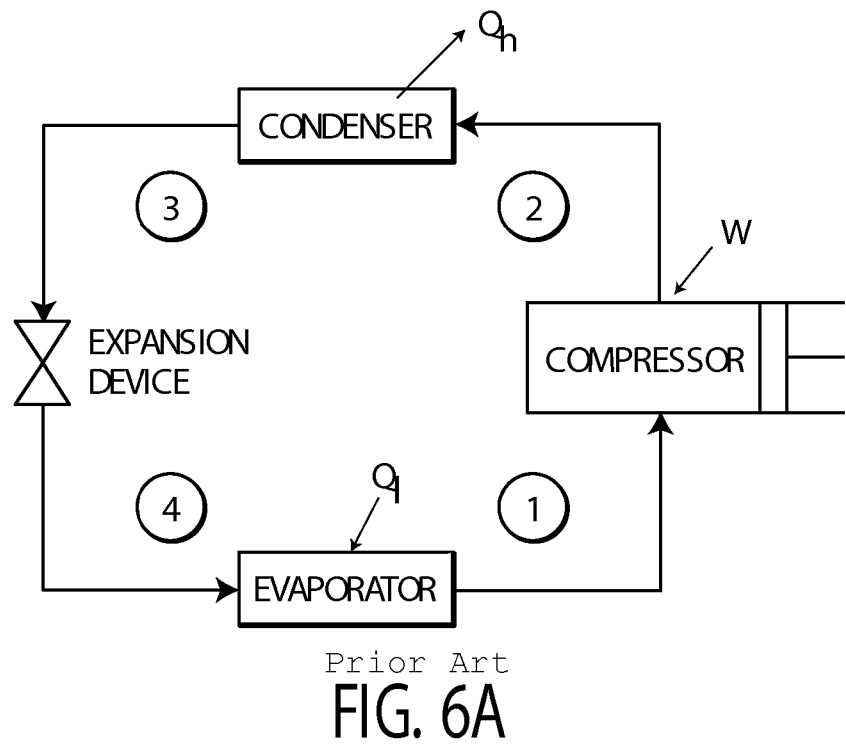
FIGS. 6A and 6B show, respectively, a schematic of a vapor compression cycle and a temperature-entropy diagram.
Figure 6B:
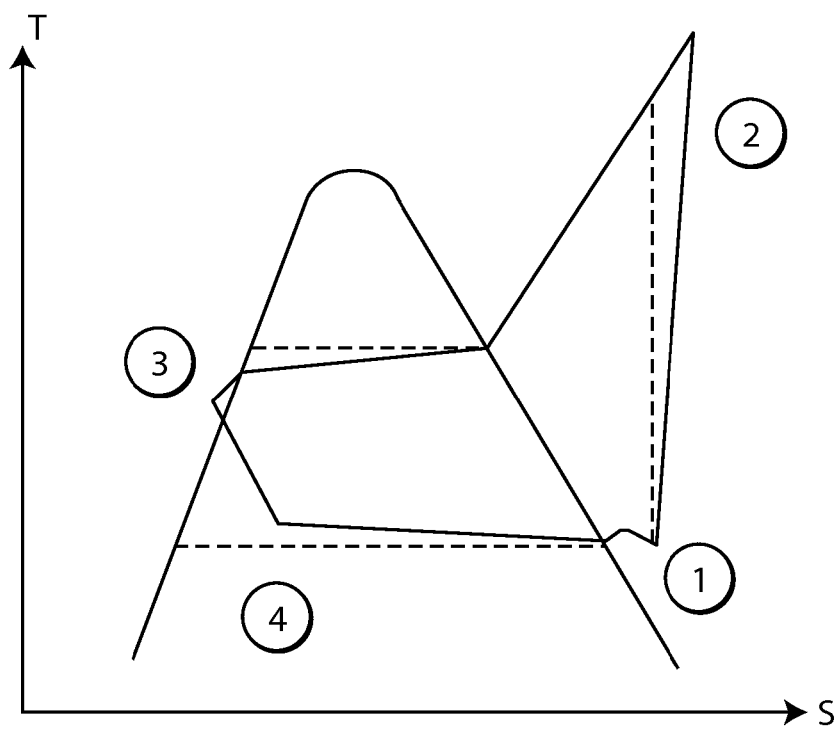

As shown in FIG. 5, the efficiency of the chiller varies with the oil concentration in the evaporator 103. Line 162 shows a non-monotonic relationship. After the relationship is determined by plotting the efficiency with respect to oil concentration, an operating regime may thereafter be defined. While typically, after oil is removed from the evaporator 103, it is not voluntarily replenished, a lower limit 160 of the operating regime defines, in a subsequent removal operation, a boundary beyond which it is not useful to extend. Complete oil removal is not only costly and directly inefficient, it may also result in reduced system efficiency. Likewise, when the oil level exceeds an upper boundary 161 of the operating regime, system efficiency drops and it is cost effective to service the chiller to restore optimum operation. Therefore, in a close loop feedback system, the distance between the lower boundary 160 and upper boundary will be much narrower than in a periodic maintenance system. The oil separator (e.g., partial distillation apparatus 105 or other type system) in a closed loop feedback system is itself typically less efficient than a larger system typically employed during periodic maintenance, so there are advantages to each type of arrangement.

Example 2

Figure 7A:
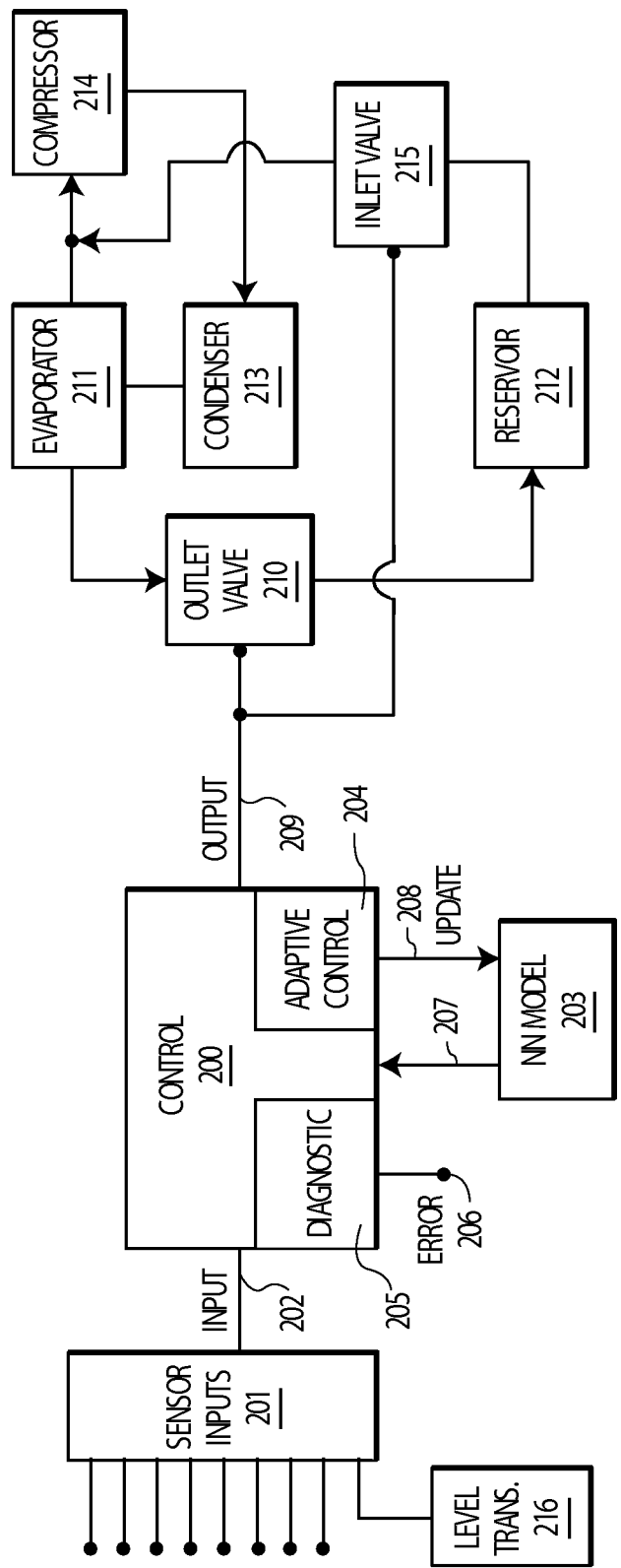
FIGS. 7A, 7B and 7C show, respectively, different block diagrams of a control according to the present invention.

FIG. 7A shows a block diagram of a first embodiment of a control system according to the present invention. In this system, refrigerant charge is controlled using an adaptive control 200, with the control receiving refrigerant charge level 216 (from a level transmitter, e.g., Henry Valve Co., Melrose Park Ill. LCA series Liquid Level Column with E-9400 series Liquid Level Switches, digital output, or K-Tek Magnetostrictive Level Transmitters AT200 or AT600, analog output), optionally system power consumption (kWatt-hours), as well as thermodynamic parameters, including condenser and evaporator water temperature in and out, condenser and evaporator water flow rates and pressure, in and out, compressor RPM, suction and discharge pressure and temperature, and ambient pressure and temperature, all through a data acquisition system for sensor inputs 201. These variables are fed into the adaptive control 200 employing a nonlinear model of the system, based on neural network 203 technology. The variables are preprocessed to produce a set of derived variables from the input set, as well as to represent temporal parameters based on prior data sets. The neural network 203 evaluates the input data set periodically, for example every 30 seconds, and produces an output control signal 209 or set of signals. After the proposed control is implemented, the actual response is compared with a predicted response based on the internal model defined by the neural network 203 by an adaptive control update subsystem 204, and the neural network is updated 205 to reflect or take into account the "error". A further output 206 of the system, from a diagnostic portion 205, which may be integrated with the neural network or separate, indicates a likely error in either the sensors and network itself, or the plant being controlled.

The controlled variable is, for example, the refrigerant charge in the system. In order to remove refrigerant, liquid refrigerant from the evaporator 211 is transferred to a storage vessel 212 through a valve 210. In order to add refrigerant, gaseous refrigerant may be returned to the compressor 214 suction, controlled by valve 215, or liquid refrigerant pumped to the evaporator 211. Refrigerant in the storage vessel 212 may be subjected to analysis and purification.

Example 3

Figure 7B:
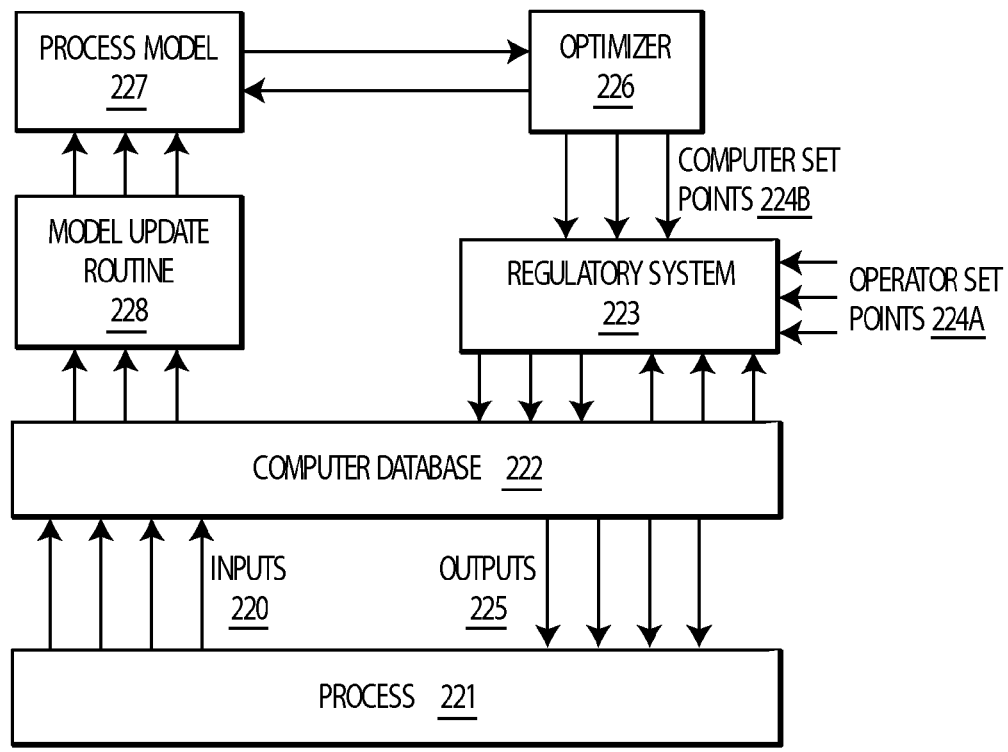

A second embodiment of the control system employs feedforward optimization control strategies, as shown in FIG. 7B. FIG. 7B shows a signal-flow block diagram of a computer-based feedforward optimizing control system. Process variables 220 are measured, checked for reliability, filtered, averaged, and stored in the computer database 222. A regulatory system 223 is provided as a front line control to keep the process variables 220 at a prescribed and desired slate of values. The conditioned set of measured variables are compared in the regulatory system 223 with the desired set points from operator 224A and optimization routine 224B. Errors detected are then used to generate control actions that are then transmitted as outputs 225 to final control elements in the process 221. Set points for the regulatory system 223 are derived either from operator input 224A or from outputs of the optimization routine 224B. Note that the optimizer 226 operates directly upon the model 227 in arriving at its optimal set-point slate 224B. Also note that the model 227 is updated by means of a special routine 228 just prior to use by the optimizer 227. The feedback update feature ensures adequate mathematical process description in spite of minor instrumentation errors and, in addition, will compensate for discrepancies arising from simplifying assumptions incorporated in the model 227. In this case, the controlled variable may be, for example, compressor speed, alone or in addition to refrigerant charge level.

The input variables are, in this case, similar to those in Example 2, including refrigerant charge level, optionally system power consumption (kWatt-hours), as well as thermodynamic parameters, including condenser and evaporator water temperature in and out, condenser and evaporator water flow rates and pressure, in and out, compressor RPM, suction and discharge pressure and temperature, and ambient pressure and temperature.

Example 4

Figure 7C:
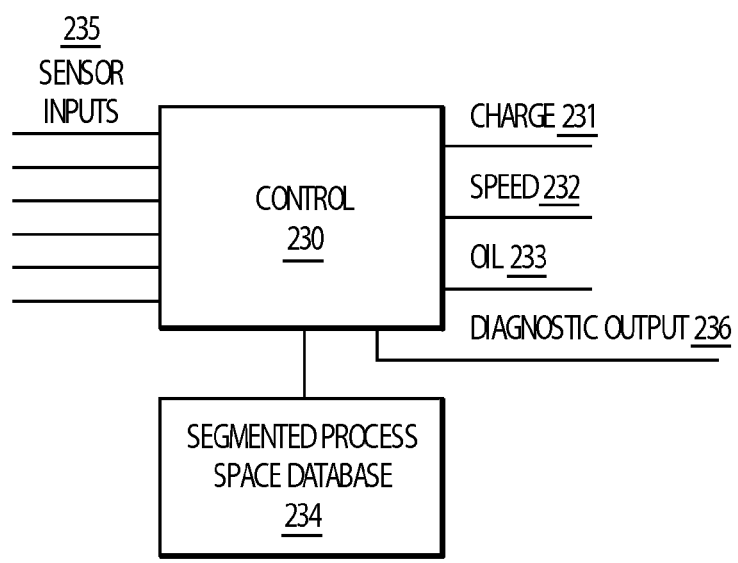
Figure 8:
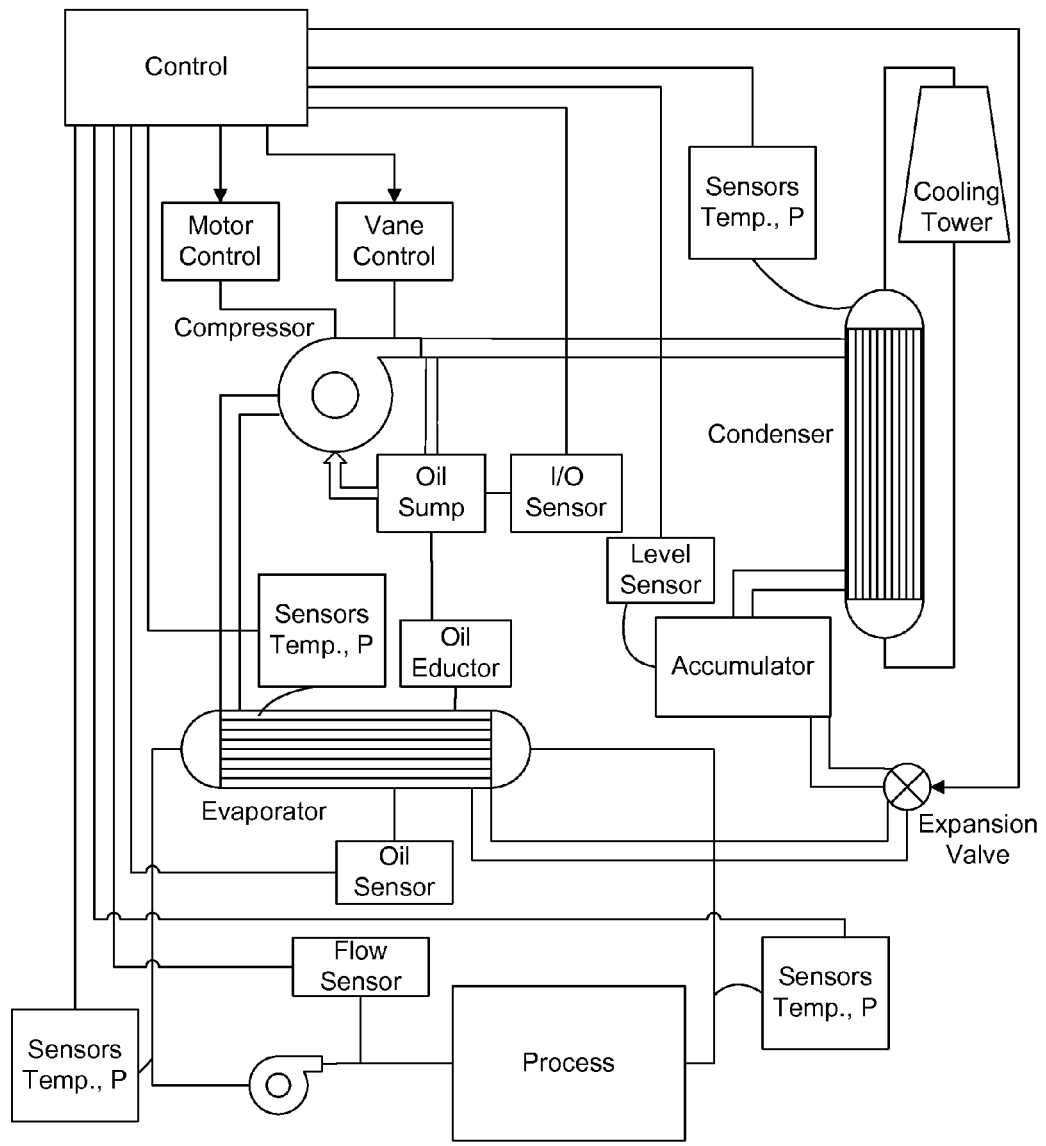
FIG. 8 shows a semi-schematic diagram of a refrigeration system controlled according to the present invention.
Figure 9:
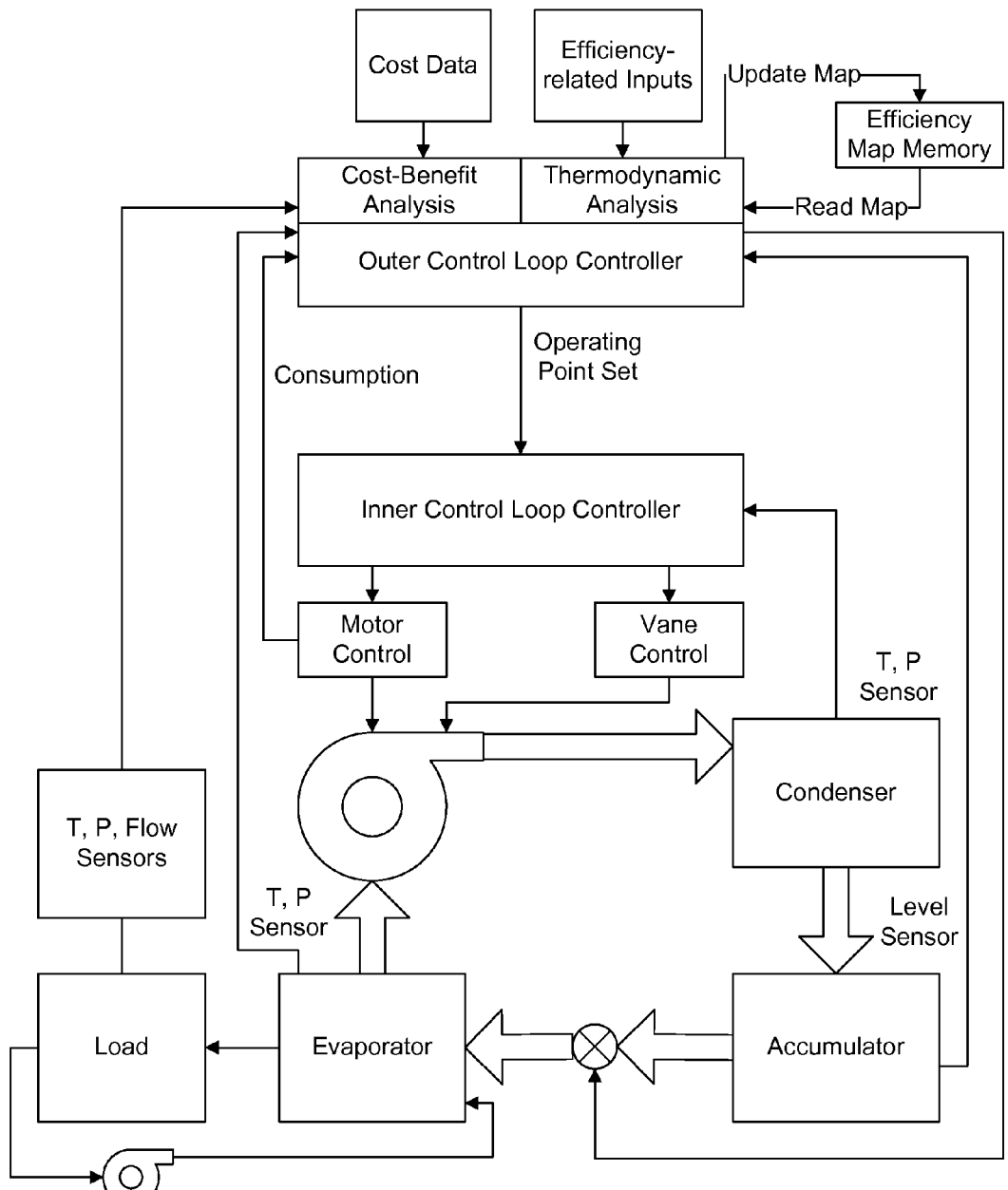
FIG. 9 shows a schematic diagram of a control for a refrigeration system according to the present invention.

As shown in FIG. 7C, a control system 230 is provided which controls refrigerant charge level 231, compressor speed 232, and refrigerant oil concentration 233 in evaporator. Instead of providing a single complex model of the system, a number of simplified relationships are provided in a database 234, which segment the operational space of the system into a number of regions or planes based on sensor inputs. The sensitivity of the control system 230 to variations in inputs 235 is adaptively determined by the control during operation, in order to optimize energy efficiency.

Data is also stored in the database 234 as to the filling density of the operational space; when the set of input parameters identifies a well populated region of the operational space, a rapid transition is effected to achieve the calculated most efficient output conditions. On the other hand, if the region of the operational space is poorly populated, the control 230 provides a slow, searching alteration of the outputs seeking to explore the operational space to determine the optimal output set. This searching procedure also serves to populate the space, so that the control 230 will avoid the naïve strategy after a few encounters.

In addition, for each region of the operational space, a statistical variability is determined. If the statistical variability is low, then the model for the region is deemed accurate, and continual searching of the local region is reduced. On the other hand, if the variability is high, the control 230 analyzes the input data set to determine a correlation between any available input 235 and the system efficiency, seeking to improve the model for that region stored in the database 234. This correlation may be detected by searching the region through sensitivity testing of the input set with respect to changes in one or more of the outputs 231, 232, 233. For each region, preferably a linear model is constructed relating the set of input variables and the optimal output variables. Alternately, a relatively simple non-linear network, such as a neural network, may be employed.

The operational regions, for example, segment the operational space into regions separated by 5% of refrigerant charge level, from −40% to +20% of design, oil content of evaporator by 0.5% from 0% to 10%, and compressor speed, from minimum to maximum in 10-100 increments. It is also possible to provide non-uniformly spaced regions, or even adaptively sized regions based on the sensitivity of the outputs to input variations at respective portions of the input space.

The control system also provides a set of special modes for system startup and shutdown. These are distinct from the normal operational modes, in that energy efficiency is not generally a primary consideration during these transitions, and because other control issues may be considered important. These modes also provide options for control system initialization and fail-safe operation.

It is noted that, since the required update time for the system is relatively long, the neural network calculations may be implemented serially on a general purpose computer, e.g., an Intel Pentium IV or Athlon XP processor running Windows XP or a real time operating system, and therefore specialized hardware (other than the data acquisition interface) is typically not necessary.

It is preferred that the control system provide a diagnostic output 236 which "explains" the actions of the control, for example identifying, for any given control decision, the sensor inputs which had the greatest influence on the output state. In neural network systems, however, it is often not possible to completely rationalize an output. Further, where the system detects an abnormal state, either in the plant being controlled or the controller itself, it is preferred that information be communicated to an operator or service engineer. This may be by way of a stored log, visual or audible indicators, telephone or Internet telecommunications, control network or local area network communications, radio frequency communication, or the like. In many instances, where a serious condition is detected and where the plant cannot be fully deactivated, it is preferable to provide a "failsafe" operational mode until maintenance may be performed.

The foregoing description of the preferred embodiment of the invention has been presented for purposes of illustration and description and is not intended to be exhaustive or to limit the invention to the precise forms disclosed, since many modifications and variations are possible in light of the above teaching. Some modifications have been described in the specifications, and others may occur to those skilled in the art to which the invention pertains.

What is claimed is:

1. A method for controlling a phase change refrigeration system having an evaporator, employing a refrigerant and a non-volatile liquid mixed with the refrigerant in at least a portion of the refrigeration system, comprising:
    storing a map relating evaporator efficiency according to a predetermined metric, evaporator heat load, refrigerant amount in the evaporator, and a concentration or amount of the non-volatile liquid mixed with the refrigerant in the evaporator; and
    selectively altering an operating point of the evaporator, by partitioning refrigerant between an accumulator and the evaporator and thereby altering a concentration of non-volatile liquid mixed with the refrigerant in the evaporator, during operation of the evaporator, by retrieving the stored map with at least one automated processor and processing data corresponding to at least a measured evaporator heat load during operation and in conjunction with the stored map, to selectively transition the operating point of the refrigeration system toward an optimum operating point.

2. The method according to claim 1, wherein the optimum operating point is a feasible operating point having a highest energy efficiency.

3. The method according to claim 1, wherein the optimum operating point is a feasible operating point having a highest operating cost efficiency.

4. The method according to claim 1, wherein the optimum operating point is a feasible operating point having a highest process economic efficiency.

5. The method according to claim 1, further comprising updating the map based on at least measurements of at least one of (a) evaporator efficiency and power consumption, and (b) evaporator heat load.

6. The method according to claim 5, wherein the map is further updated based on at least a measurement of refrigerant in the evaporator.

7. The method according to claim 5, wherein the map is further updated based on at least a measurement of non-volatile liquid in the evaporator.

8. The method according to claim 1, wherein the non-volatile liquid mixed with the refrigerant in the evaporator comprises lubricating oil.

9. The method according to claim 1, wherein said selectively altering comprises controlling a flow of refrigerant into the evaporator to dynamically ensure sufficient cooling capacity to meet cooling demand, and to deviate from a steady state level of refrigerant in the evaporator to move toward a level corresponding to the optimum operating point.

10. The method according to claim 1, further comprising performing a thermodynamic analysis to determine a need to remove non-volatile liquid from the evaporator.

11. The method according to claim 1, further comprising performing a cost-benefit analysis to determine an optimal time to remove a portion of the non-volatile refrigerant from the evaporator, dependent on a cost associated with a removal of non-volatile refrigerant from the evaporator.

12. The method according to claim 1, further comprising performing a cost-benefit analysis to control removal of a portion of the non-volatile refrigerant from the evaporator, dependent on at least a cost of a removal of non-volatile refrigerant from the evaporator, a power consumption cost of operating the refrigeration system, and a benefit resulting from a process cooled by the evaporator.

13. A refrigeration system comprising:
- a compressor configured to compress a refrigerant;
- a condenser configured to condense refrigerant to a liquid, lubricated with a non-volatile liquid;
- an accumulator configured to store a variable portion of the condensed refrigerant;
- an evaporator configured to remove heat from a process by evaporation of the condensed refrigerant, having a variable amount of refrigerant gas, and subject to accretion of the non-volatile liquid which migrates from the compressor; and
- a controller, having a memory configured to store a relationship of at least evaporator efficiency, evaporator heat load, refrigerant amount in the evaporator, and a variable dependent on the non-volatile liquid in the evaporator, an input corresponding to at least a measured evaporator heat load during operation, and an output computed during operation of the refrigeration system, configured to selectively alter an operating point of the evaporator, by partitioning refrigerant between the accumulator and the evaporator and thereby changing the variable, and in dependence on a contents of the memory, and the input corresponding to at least a measured evaporator heat load during operation, to selectively move toward an optimum operating point.

14. The refrigeration system according to claim 13, wherein the optimum operating point is a feasible operating point selected from the group consisting of an operating point having a highest energy efficiency, a highest operating cost efficiency, and a highest process economic efficiency.

15. The refrigeration system according to claim 13, wherein the control is further configured to update the memory based on at least (a) measurements of at least one of evaporator efficiency and power consumption, and (b) evaporator heat load.

16. The refrigeration system according to claim 15, wherein the control is further configured to update the memory based on at least a measurement of refrigerant in the evaporator.

17. The refrigeration system according to claim 15, wherein the control is further configured to update the memory based on at least a measurement of non-volatile liquid in the evaporator.

18. The refrigeration system according to claim 13, wherein the control is configured to selectively alter a flow of refrigerant into the evaporator to dynamically ensure sufficient cooling capacity to meet cooling demand, and to deviate from a steady state level of refrigerant in the evaporator to move toward a level corresponding to the optimum operating point.

19. The refrigeration system according to claim 13, wherein the control is configured to perform a thermodynamic analysis to determine an optimum time to remove non-volatile liquid from the evaporator.

20. A control system for controlling a refrigeration system having an operating point, comprising:
- a memory configured to store a relationship of at least an evaporator efficiency, an evaporator heat load, a refrigerant amount in the evaporator, and a variable dependent on a non-volatile liquid mixed with refrigerant in the evaporator;
- an input port configured to receive a signal corresponding to at least a measured evaporator heat load during operation;
- an output port configured to present an output to selectively alter an operating point of the evaporator, by altering the refrigerant amount in the evaporator and thereby changing the variable; and
- a processor, configured to receive the signal, access the memory; and generate the output to selectively move toward an optimum operating point.

* * * * *